US010610332B2

(12) United States Patent
Wu et al.

(10) Patent No.: US 10,610,332 B2
(45) Date of Patent: Apr. 7, 2020

(54) ADJUSTMENT OF TOOTH POSITION IN A VIRTUAL DENTAL MODEL

(71) Applicant: Align Technology, Inc., San Jose, CA (US)

(72) Inventors: Fuming Wu, Pleasanton, CA (US); Vadim Matov, San Jose, CA (US); Artem Borovinskih, San Jose, CA (US); Rene M. Sterental, Palo Alto, CA (US); Pavel Agapov, Palo Alto, CA (US); Anton Spiridonov, Moscow (RU); Anatoliy Boltunov, Moscow (RU)

(73) Assignee: Align Technology, Inc., San Jose, CA (US)

(*) Notice: Subject to any disclaimer, the term of this patent is extended or adjusted under 35 U.S.C. 154(b) by 452 days.

(21) Appl. No.: 15/227,401

(22) Filed: Aug. 3, 2016

(65) Prior Publication Data
US 2016/0338799 A1    Nov. 24, 2016

Related U.S. Application Data

(62) Division of application No. 13/477,879, filed on May 22, 2012, now Pat. No. 9,414,897.

(51) Int. Cl.
*G01N 33/48* (2006.01)
*A61C 7/00* (2006.01)
*G06T 19/20* (2011.01)
*G06F 17/50* (2006.01)
*G06G 7/58* (2006.01)
*G06F 19/00* (2018.01)

(52) U.S. Cl.
CPC .............. *A61C 7/002* (2013.01); *G06F 17/50* (2013.01); *G06T 19/20* (2013.01); *A61C 2007/004* (2013.01); *G06F 19/34* (2013.01); *G06T 2210/41* (2013.01)

(58) Field of Classification Search
None
See application file for complete search history.

(56) References Cited

U.S. PATENT DOCUMENTS

| | | |
|---|---|---|
| 2,171,695 A | 9/1939 | Harper |
| 2,194,790 A | 3/1940 | Gluck |
| 2,467,432 A | 4/1949 | Kesling |
| 2,531,222 A | 11/1950 | Kesling |
| 3,089,487 A | 5/1963 | Enicks et al. |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,055,895 A | 11/1977 | Huge |
| 4,117,596 A | 10/1978 | Wallshein |
| 4,139,944 A | 2/1979 | Bergersen |
| 4,179,811 A | 12/1979 | Hinz |
| 4,183,141 A | 1/1980 | Dellinger |
| 4,195,046 A | 3/1980 | Kesling |
| 4,253,828 A | 3/1981 | Coles et al. |

(Continued)

FOREIGN PATENT DOCUMENTS

| | | |
|---|---|---|
| AU | 517102 B | 11/1977 |
| AU | 3031677 A | 11/1977 |

(Continued)

OTHER PUBLICATIONS

US 8,553,966 B1, 10/2013, Alpern et al. (withdrawn)
Bernabe et al.; Are the lower incisors the best predictors for the unerupted canine and premolars sums? An analysis of peruvian sample; The Angle Orthodontist; 75(2); pp. 202-207; Mar. 2005.
Collins English Dictionary; Teeth (definition); 9 pages; retrieved from the internet (https:www.collinsdictionary.com/us/dictionary/english/teeth) on May 13, 2019.
dictionary.com; Plural (definition); 6 pages; retrieved from the internet ( https://www.dictionary.com/browse/plural#) on May 13, 2019.
dictionary.com; Quadrant (definition); 6 pages; retrieved from the internet ( https://www.dictionary.com/browse/quadrant?s=t) on May 13, 2019.

(Continued)

*Primary Examiner* — Eric S Dejong
(74) *Attorney, Agent, or Firm* — Shay Glenn LLP

(57) ABSTRACT

The present disclosure provides computing device implemented methods, computing device readable media, and systems for adjustment of tooth position in a virtual dental model. Virtual dental modeling can include detecting space and/or collision between posterior teeth of an upper jaw and posterior teeth of a lower jaw in a virtual dental model that has been set in a preliminary target position. An energy function can be defined including the space and/or collision, tooth root movement, and align points. Weights can be assigned for each variable in the energy function. A position of the posterior teeth of the upper jaw and the posterior teeth of the lower jaw can be adjusted in six degrees of freedom to minimize the energy function. The detection, definition, assignment, and adjustment can be repeated until the energy function converges. The weights can be adjusted to reduce the space and/or collision.

20 Claims, 11 Drawing Sheets

(56) References Cited

U.S. PATENT DOCUMENTS

| | | |
|---|---|---|
| 4,255,138 A | 3/1981 | Frohn |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,478,580 A | 10/1984 | Barrut |
| 4,500,294 A | 2/1985 | Lewis |
| 4,505,673 A | 3/1985 | Yoshii |
| 4,519,386 A | 5/1985 | Sullivan |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,061,839 A | 10/1991 | Matsuno et al. |
| 5,083,919 A | 1/1992 | Quachi |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |

(56) References Cited

U.S. PATENT DOCUMENTS

| | | |
|---|---|---|
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 6,002,706 A | 12/1999 | Staver et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,217,334 B1 | 4/2001 | Hultgren |
| 6,227,850 B1 | 5/2001 | Chishti et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |

(56) References Cited

U.S. PATENT DOCUMENTS

| | | |
|---|---|---|
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,984,128 B2 | 1/2006 | Breining et al. |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,217,131 B2 | 5/2007 | Vuillemot |
| 7,220,122 B2 | 5/2007 | Chishti |
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,837,469 B2 | 10/2010 | Chishti et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,045,772 B2 | 10/2011 | Kosuge et al. |
| 8,054,556 B2 | 11/2011 | Chen et al. |

(56) References Cited

U.S. PATENT DOCUMENTS

| | | |
|---|---|---|
| 8,070,490 B1 | 12/2011 | Roetzer et al. |
| 8,075,306 B2 | 12/2011 | Kitching et al. |
| 8,077,949 B2 | 12/2011 | Liang et al. |
| 8,083,556 B2 | 12/2011 | Stadler et al. |
| D652,799 S | 1/2012 | Mueller |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,108,189 B2 | 1/2012 | Chelnokov et al. |
| 8,118,592 B2 | 2/2012 | Tortorici |
| 8,126,025 B2 | 2/2012 | Takeda |
| 8,144,954 B2 | 3/2012 | Quadling et al. |
| 8,160,334 B2 | 4/2012 | Thiel et al. |
| 8,172,569 B2 | 5/2012 | Matty et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,275,180 B2 | 9/2012 | Kuo |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,401,826 B2 | 3/2013 | Cheng et al. |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,738,394 B2 | 5/2014 | Kuo |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kou |
| 8,956,058 B2 | 2/2015 | Rösch |
| 8,992,216 B2 | 3/2015 | Karazivan |
| 9,004,915 B2 | 4/2015 | Moss et al. |
| 9,022,792 B2 | 5/2015 | Sticker et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,242,118 B2 | 1/2016 | Brawn |
| 9,277,972 B2 | 3/2016 | Brandt et al. |
| 9,336,336 B2 | 5/2016 | Deichmann et al. |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,444,981 B2 | 9/2016 | Bellis et al. |
| 9,463,287 B1 | 10/2016 | Lorberbaum et al. |
| 9,492,243 B2 | 11/2016 | Kuo |
| 9,506,808 B2 | 11/2016 | Jeon et al. |
| 9,510,918 B2 | 12/2016 | Sanchez |
| 9,566,132 B2 | 2/2017 | Stone-Collonge et al. |
| 9,584,771 B2 | 2/2017 | Mandelis et al. |
| 9,589,329 B2 | 3/2017 | Levin |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 10,123,706 B2 | 11/2018 | Elbaz et al. |
| 10,123,853 B2 | 11/2018 | Moss et al. |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,248,883 B2 | 4/2019 | Borovinskih et al. |
| 10,258,432 B2 | 4/2019 | Webber |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029068 A1 | 2/2004 | Sachdeva et al. |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |

(56) References Cited

U.S. PATENT DOCUMENTS

| | | |
|---|---|---|
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0042569 A1 | 2/2005 | Plan et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0215582 A1 | 9/2007 | Roeper et al. |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1 | 3/2008 | Park et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118886 A1 | 5/2008 | Liang et al. |
| 2008/0141534 A1 | 6/2008 | Hilliard |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0181346 A1 | 7/2009 | Orth |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0316966 A1 | 12/2009 | Marshall et al. |
| 2009/0317757 A1 | 12/2009 | Lemchen |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0068676 A1 | 3/2010 | Mason et al. |
| 2010/0086890 A1 | 4/2010 | Kuo |

(56) References Cited

U.S. PATENT DOCUMENTS

| | | |
|---|---|---|
| 2010/0138025 A1 | 6/2010 | Morton et al. |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0279243 A1 | 11/2010 | Cinader et al. |
| 2010/0280798 A1 | 11/2010 | Pattijn et al. |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0143300 A1 | 6/2011 | Villaalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0029883 A1 | 2/2012 | Heinz et al. |
| 2012/0040311 A1 | 2/2012 | Nilsson |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0201488 A1 | 8/2013 | Ishihara |
| 2013/0204599 A1 | 8/2013 | Matov et al. |
| 2013/0209952 A1 | 8/2013 | Kuo et al. |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0278396 A1 | 10/2013 | Kimmel |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0325431 A1 | 12/2013 | See et al. |
| 2013/0337412 A1 | 12/2013 | Kwon |
| 2014/0081091 A1 | 3/2014 | Abolfathi et al. |
| 2014/0136222 A1 | 5/2014 | Arnone et al. |
| 2014/0142902 A1 | 5/2014 | Chelnokov et al. |
| 2014/0280376 A1 | 9/2014 | Kuo |
| 2014/0294273 A1 | 10/2014 | Jaisson |
| 2015/0002649 A1 | 1/2015 | Nowak et al. |
| 2015/0004553 A1 | 1/2015 | Li et al. |
| 2015/0079531 A1 | 3/2015 | Heine |
| 2015/0094564 A1 | 4/2015 | Tashman et al. |
| 2015/0132708 A1 | 5/2015 | Kuo |
| 2015/0173856 A1 | 6/2015 | Iowe et al. |
| 2015/0182303 A1 | 7/2015 | Abraham et al. |
| 2015/0230885 A1 | 8/2015 | Wucher |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2016/0003610 A1 | 1/2016 | Lampert et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0246936 A1 | 8/2016 | Kahn |
| 2016/0287358 A1 | 10/2016 | Nowak et al. |
| 2016/0302885 A1 | 10/2016 | Matov et al. |
| 2016/0367339 A1 | 12/2016 | Khardekar et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0071705 A1 | 3/2017 | Kuo |
| 2017/0100212 A1 | 4/2017 | Sherwood et al. |
| 2017/0100213 A1 | 4/2017 | Kuo |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0319296 A1 | 11/2017 | Webber et al. |
| 2018/0000563 A1 | 1/2018 | Shanjani et al. |
| 2018/0000565 A1 | 1/2018 | Shanjani et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071055 A1 | 3/2018 | Kuo |
| 2018/0096465 A1 | 4/2018 | Levin |
| 2018/0125610 A1 | 5/2018 | Carrier et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |
| 2018/0280118 A1 | 10/2018 | Cramer |
| 2018/0284727 A1 | 10/2018 | Cramer et al. |
| 2018/0318043 A1 | 11/2018 | Li et al. |
| 2018/0353264 A1 | 12/2018 | Riley et al. |
| 2018/0360567 A1 | 12/2018 | Xue et al. |
| 2018/0368944 A1 | 12/2018 | Sato et al. |
| 2018/0368961 A1 | 12/2018 | Shanjani et al. |
| 2019/0019187 A1 | 1/2019 | Miller et al. |
| 2019/0021817 A1 | 1/2019 | Sato et al. |
| 2019/0029522 A1 | 1/2019 | Sato et al. |
| 2019/0029784 A1 | 1/2019 | Moalem et al. |
| 2019/0046296 A1 | 2/2019 | Kopelman et al. |
| 2019/0046297 A1 | 2/2019 | Kopelman et al. |
| 2019/0069975 A1 | 3/2019 | Cam et al. |
| 2019/0076026 A1 | 3/2019 | Elbaz et al. |
| 2019/0076214 A1 | 3/2019 | Nyukhtikov et al. |
| 2019/0076216 A1 | 3/2019 | Moss et al. |
| 2019/0090983 A1 | 3/2019 | Webber et al. |

(56) References Cited

U.S. PATENT DOCUMENTS

| | | |
|---|---|---|
| 2019/0095539 A1 | 3/2019 | Elbaz et al. |
| 2019/0099129 A1 | 4/2019 | Kopelman et al. |

FOREIGN PATENT DOCUMENTS

| | | |
|---|---|---|
| CA | 1121955 A1 | 4/1982 |
| CN | 1655732 A | 8/2005 |
| CN | 1655733 A | 8/2005 |
| CN | 102017658 A | 4/2011 |
| CN | 103889364 A | 6/2014 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| ES | 463897 A1 | 1/1980 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 04-028359 A | 1/1992 |
| JP | 08-508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| JP | 2013192865 A | 9/2013 |
| KR | 10-20020062793 A | 7/2002 |
| KR | 10-20090065778 A | 6/2009 |
| TW | 480166 B | 3/2002 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO98/032394 A1 | 7/1998 |
| WO | WO98/044865 A1 | 10/1998 |
| WO | WO01/08592 A1 | 2/2001 |
| WO | WO01/85047 A2 | 11/2001 |
| WO | WO02/017776 A2 | 3/2002 |
| WO | WO02/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/059988 A1 | 5/2010 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/083968 A1 | 6/2012 |
| WO | WO2012/140021 A2 | 10/2012 |
| WO | WO2013/058879 A2 | 4/2013 |

OTHER PUBLICATIONS

Martinelli et al.; Prediction of lower permanent canine and premolars width by correlation methods; The Angle Orthodontist; 75(5); pp. 805-808; Sep. 2005.

Nourallah et al.; New regression equations for predicting the size of unerupted canines and premolars in a contemporary population; The Angle Orthodontist; 72(3); pp. 216-221; Jun. 2002.

Paredes et al.; A new, accurate and fast digital method to predict unerupted tooth size; The Angle Orthodontist; 76(1); pp. 14-19; Jan. 2006.

AADR. American Association for Dental Research; Summary of Activities; Los Angeles, CA; p. 195; Mar. 20-23,(year of pub. sufficiently earlier than effective US filing date and any foreign priority date) 1980.

Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.

Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filing date and any foreign priority date); 1998.

Allesee Orthodontic Appliances: DuraClearTM; Product information; 1 page; (year of pub. sufficiently earlier than effective US filing date and any foreign priority date) 1997.

Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

Allesee Orthodontic Appliances; The Choice Is Clear: Red, White & Blue . . . The Simple, Affordable, No-Braces Treatment; (product information), 6 pages; (year of pub. sufficiently earlier than effective US filing date and any foreign priority date) 2003.

Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.

Allesee Orthodontic Appliances; The Red, White & Blue Way to Improve Your Smile; (information for patients), 2 pages; (year of pub. sufficiently earlier than effective US filing date and any foreign priority date) 1992.

(56) References Cited

OTHER PUBLICATIONS

Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Begole et al.; A Computer System for the Analysis of Dental Casts; The Angle Orthodontist; 51(3); pp. 252-258; Jul. 1981.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(1); pp. 28-36; Jan. 1970.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bourke, Coordinate System Transformation; 1 page; retrived from the internet (http://astronomy.swin.edu.au/ pbourke/prolection/coords) on Nov. 5, 2004; Jun. 1996.

Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on The Uses of the Computer in Orthodontic Practice (Part 1); Journal of Clinical Orthodontics; 13(7); pp. 442-453; (interview); Jul. 1979.
Burstone; Dr. Charles J. Burstone on The Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret A Man With A Vision, Part 3: The Computer Gives New Vision—Literally, Part 4: Bytes 'N Bites The Computer Moves From The Front Desk To The Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental Ag; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.

(56) References Cited

OTHER PUBLICATIONS

Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.
Di Muzio et al.; Minimum intensity projection (MinIP); 6 pages; retrieved from the internet (https://radiopaedia.org/articles/minimum-intensity-projection-minip) on Sep. 6, 2018.
Doruk et al.; The role of the headgear timer in extraoral co-operation; European Journal of Orthodontics; 26; pp. 289-291; Jun. 1, 2004.
Doyle; Digital Dentistry; Computer Graphics World; pp. 50-52 and p. 54; Oct. 2000.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Friede et al.; Accuracy of Cephalometric Prediction in Orthognathic Surgery; Journal of Oral and Maxillofacial Surgery; 45(9); pp. 754-760; Sep. 1987.
Friedrich et al; Measuring system for in vivo recording of force systems in orthodontic treatment—concept and analysis of accuracy; J. Biomech.; 32(1); pp. 81-85; (Abstract Only) Jan. 1999.
Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.
Gao et al.; 3-D element Generation for Multi-Connected Complex Dental and Mandibular Structure; IEEE Proceedings International Workshop in Medical Imaging and Augmented Reality; pp. 267-271; Jun. 12, 2001.
Gim-Alldent Deutschland, "Das DUX System: Die Technik," 3 pages; (English Translation Included); (year of pub. sufficiently earlier than effective US filing date and any foreign priority date); 2002.
Gottleib et al.; JCO Interviews Dr. James A. McNamara, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.
Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.
Grest, Daniel; Marker-Free Human Motion Capture in Dynamic Cluttered Environments from a Single View-Point, PhD Thesis; 171 pages; Dec. 2007.
Guess et al.; Computer Treatment Estimates In Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.
Highbeam Research; Simulating stress put on jaw. (Ansys Inc.'s finite element analysis software); 2 pages; retrieved from the Internet (http://static.highbeam.com/t/toolingampproduction/november011996/simulatingstressputonfa . . . ); on Nov. 5, 2004.
Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.
Hoffmann et al.; Role of Cephalometry for Planning of Jaw Orthopedics and Jaw Surgery Procedures; Informatbnen, pp. 375-396; (English Abstract Included); Mar. 1991.
Hojjatie et al.; Three-Dimensional Finite Element Analysis of Glass-Ceramic Dental Crowns; Journal of Biomechanics; 23(11); pp. 1157-1166; Jan. 1990.
Huckins; CAD-CAM Generated Mandibular Model Prototype from MRI Data; AAOMS, p. 96; (Abstract Only); (year of pub. sufficiently earlier than effective US filing date and any foreign priority date) 1999.
Invisalign; You were made to move. There's never been a better time to straighten your teeth with the most advanced clear aligner in the world; Product webpage; 2 pages; retrieved from the internet (www.invisalign.com/) on Dec. 28, 2017.
JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.
JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.
Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.
Kanazawa et al.; Three-Dimensional Measurements of the Occlusal Surfaces of Upper Molars in a Dutch Population; Journal of Dental Research; 63(11); pp. 1298-1301; Nov. 1984.
Kesling et al.; The Philosophy of the Tooth Positioning Appliance; American Journal of Orthodontics and Oral surgery; 31(6); pp. 297-304; Jun. 1945.
Kesling; Coordinating the Predetermined Pattern and Tooth Positioner with Conventional Treatment; American Journal of Orthodontics and Oral Surgery; 32(5); pp. 285-293; May 1946.
Kleeman et al.; The Speed Positioner; J. Clin. Orthod.; 30(12); pp. 673-680; Dec. 1996.
Kochanek; Interpolating Splines with Local Tension, Continuity and Bias Control; Computer Graphics; 18(3); pp. 33-41; Jan. 1, 1984.
Kumar et al.; Rapid maxillary expansion: A unique treatment modality in dentistry; J. Clin. Diagn. Res.; 5(4); pp. 906-911; Aug. 2011.
Kunii et al.; Articulation Simulation for an Intelligent Dental Care System; Displays; 15(3); pp. 181-188; Jul. 1994.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

(56) References Cited

OTHER PUBLICATIONS

Leinfelder et al.; A New Method for Generating Ceramic Restorations: a CAD-CAM System; Journal of the American Dental Association; 118(6); pp. 703-707; Jun. 1989.
Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.
Mccann; Inside the ADA; J. Amer. Dent. Assoc, 118:286-294; Mar. 1989.
Mcnamara et al.; Invisible Retainers; J. Clin Orthod.; pp. 570-578; 11 pages; (Author Manuscript); Aug. 1985.
Mcnamara et al.; Orthodontic and Orthopedic Treatment in the Mixed Dentition; Needham Press; pp. 347-353; Jan. 1993.
Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.
Moles; Correcting Mild Malalignments—As Easy As One, Two, Three; AOA/Pro Corner; 11(2); 2 pages; (year of pub. sufficiently earlier than effective US filing date and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.
Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
ormco.com; Increasing clinical performance with 3D interactive treatment planning and patient-specific appliances; 8 pages; retrieved from the internet (http://www.konsident.com/wp-content/files_mf/1295385693http___ormco.com_index_cmsfilesystemaction_fileOrmcoPDF_whitepapers.pdf) on Feb. 27, 2019.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages , Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.

Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD/CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 1990.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Siemens; Cerec—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Sirona Dental Systems GmbH, Cerec 3D, Manuel utiiisateur, Version 2.0X (in French); 114 pages; (English translation of table of

(56) References Cited

OTHER PUBLICATIONS contents included); (year of pub. sufficiently earlier than effective US filing date and any foreign priority date); 2003.

Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.

Sturman; Interactive Keyframe Animation of 3-D Articulated Models; Proceedings Graphics Interface '84; vol. 86; pp. 35-40; May-Jun. 1984.

The American Heritage, Stedman's Medical Dictionary; Gingiva; 3 pages; retrieved from the interent (http://reference.com/search/search?q=gingiva) on Nov. 5, 2004.

Thera Mon; "Microsensor"; 2 pages; retrieved from the internet (www.english.thera-mon.com/the-product/transponder/index.html); on Sep. 19, 2016.

Thorlabs; Pellin broca prisms; 1 page; retrieved from the internet (www.thorlabs.com); Nov. 30, 2012.

Tiziani et al.; Confocal principle for macro and microscopic surface and defect analysis; Optical Engineering; 39(1); pp. 32-39; Jan. 1, 2000.

Truax; Truax Clasp-Less(TM) Appliance System; The Functional Orthodontist; 9(5); pp. 22-24, 26-8; Sep.-Oct. 1992.

Tru-Tatn Orthodontic & Dental Supplies, Product Brochure, Rochester, Minnesota 55902, 16 pages; (year of pub. sufficiently earlier than effective US filing date and any foreign priority date) 1996.

U.S. Department of Commerce, National Technical Information Service, Holodontography: An Introduction to Dental Laser Holography; School of Aerospace Medicine Brooks AFB Tex; Mar. 1973, 40 pages; Mar. 1973.

U.S. Department of Commerce, National Technical Information Service; Automated Crown Replication Using Solid Photography SM; Solid Photography Inc., Melville NY,; 20 pages; Oct. 1977.

Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.

Van Der Linden et al.; Three-Dimensional Analysis of Dental Casts by Means of the Optocom; Journal of Dental Research; 51(4); p. 1100; Jul.-Aug. 1972.

Van Der Linden; A New Method to Determine Tooth Positions and Dental Arch Dimensions; Journal of Dental Research; 51(4); p. 1104; Jul.-Aug. 1972.

Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.

Varady et al.; Reverse Engineering of Geometric ModelsAn Introduction; Computer-Aided Design; 29(4); pp. 255-268; 20 pages; (Author Manuscript); Apr. 1997.

Verstreken et al.; An Image-Guided Planning System for Endosseous Oral Implants; IEEE Transactions on Medical Imaging; 17(5); pp. 842-852; Oct. 1998.

Video of DICOM to Surgical Guides; [Copy Not Enclosed], Can be viewed at <URL:https://youtu.be/47KtOmCEFQk; Published Apr. 4, 2016.

Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.

Warunek et.al.; Clinical Use of Silicone Elastomer Applicances; JCO; 23(10); pp. 694-700; Oct. 1989.

Watson et al.; Pressures recorded at te denture base-mucosal surface interface in complete denture wearers; Journal of Oral Rehabilitation 14(6); pp. 575-589; Nov. 1987.

Wells; Application of the Positioner Appliance in Orthodontic Treatment; American Journal of Orthodontics; 58(4); pp. 351-366; Oct. 1970.

Wikipedia; Palatal expansion; 3 pages; retrieved from the internet (https://en.wikipedia.org/wiki/Palatal_expansion) on Mar. 5, 2018.

Williams; Dentistry and CAD/CAM: Another French Revolution; J. Dent. Practice Admin.; 4(1); pp. 2-5 Jan./Mar. 1987.

Williams; The Switzerland and Minnesota Developments in CAD/CAM; Journal of Dental Practice Administration; 4(2); pp. 50-55; Apr./Jun. 1987.

Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.

Witt et al.; The wear-timing measuring device in orthodontics—cui bono? Reflections on the state-of-the-art in wear-timing measurement and compliance research in orthodontics; Fortschr Kieferorthop.; 52(3); pp. 117-125; (Translation Included) Jun. 1991.

Wolf; Three-dimensional structure determination of semi-transparent objects from holographic data; Optics Communications; 1(4); pp. 153-156; Sep. 1969.

WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.

Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.

Yamada et al.; Simulation of fan-beam type optical computed-tomography imaging of strongly scattering and weakly absorbing media; Applied Optics; 32(25); pp. 4808-4814; Sep. 1, 1993.

Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.

Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.

Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.

Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.

Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.

Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.

Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.

Zhou et al.; Bio-logic analysis of injury biomarker patterns in human serum samples; Talanta; 83(3); pp. 955-959; Jan. 15, 2011.

Zhou et al.; Biofuel cells for self-powered electrochemical biosensing and logic biosensing: A review; Electroanalysis; 24(2); pp. 197-209; Feb. 2012.

Grove et al.; U.S. Appl. No. 15/726,243 entitled "Interproximal reduction templates," filed Oct. 5, 2017.

Morton et al.; U.S. Appl. No. 16/177,067 entitled "Dental appliance having selective occlusal loading and controlled intercuspation," filed Oct. 31, 2018.

Akopov et al.; U.S. Appl. No. 16/178,491 entitled "Automatic treatment planning," filed Nov. 1, 2018.

O'Leary et al.; U.S. Appl. No. 16/195,701 entitled "Orthodontic retainers," filed Nov. 19, 2018.

Shanjani et al., U.S. Appl. No. 16/206,894 entitled "Sensors for monitoring oral appliances," filed Nov. 28, 2019.

(56) References Cited

OTHER PUBLICATIONS

Shanjani et al., U.S. Appl. No. 16/231,906 entitled "Augmented reality enhancements for dental practitioners." filed Dec. 24, 2018.
Kopleman et al., U.S. Appl. No. 16/220,381 entitled "Closed loop adaptive orthodontic treatment methods and apparatuses," filed Dec. 14, 2018.
Sabina et al., U.S. Appl. No. 16/258,516 entitled "Diagnostic intraoral scanning" filed Jan. 25, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Li et al.; U.S. Appl. No. 16/171,159 entitled "Alternative bite adjustment structures," filed Oct. 25, 2018.
Culp; U.S. Appl. No. 16/236,220 entitled "Laser cutting," filed Dec. 28, 2018.
Culp; U.S. Appl. No. 16/265,287 entitled "Laser cutting," filed Feb. 1, 2019.
beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.
Berland; The use of smile libraries for cosmetic dentistry; Dental Tribunne: Asia pacfic Edition; pp. 16-18; Mar. 29, 2006.
Bookstein; Principal warps: Thin-plate splines and decomposition of deformations; IEEE Transactions on pattern analysis and machine intelligence; 11(6); pp. 567-585; Jun. 1989.
Cadent Inc.; OrthoCAD ABO user guide; 38 pages; Dec. 21, 2005.
Cadent Inc.; Reviewing and modifying an orthoCAD case; 4 pages; Feb. 14, 2005.
Daniels et al.; The development of the index of complexity outcome and need (ICON); British Journal of Orthodontics; 27(2); pp. 149-162; Jun. 2000.
Dentrix; Dentrix G3, new features; 2 pages; retrieved from the internet (http://www.dentrix.com/g3/new_features/index.asp); on Jun. 6, 2008.
Di Giacomo et al.; Clinical application of sterolithographic surgical guides for implant placement: Preliminary results; Journal Periodontolgy; 76(4); pp. 503-507; Apr. 2005.
Gansky; Dental data mining: potential pitfalls and practical issues; Advances in Dental Research; 17(1); pp. 109-114; Dec. 2003.
Geomagic; Dental reconstruction; 1 page; retrieved from the internet (http://geomagic.com/en/solutions/industry/detal_desc.php) on Jun. 6, 2008.
Gottschalk et al.; OBBTree: A hierarchical structure for rapid interference detection; 12 pages; (http://www.cs.unc.edu/?geom/OBB/OBBT.html); retieved from te internet (https://www.cse.iitk.ac.in/users/amit/courses/RMP/presentations/dslamba/presentation/sig96.pdf) on Apr. 25, 2019.
gpsdentaire.com; Get a realistic smile simulation in 4 steps with GPS; a smile management software; 10 pages; retrieved from the internet (http://www.gpsdentaire.com/en/preview/) on Jun. 6, 2008.
Karaman et al.; A practical method of fabricating a lingual retainer; Am. Journal of Orthodontic and Dentofacial Orthopedics; 124(3); pp. 327-330; Sep. 2003.
Mantzikos et al.; Case report: Forced eruption and implant site development; The Angle Orthodontist; 68(2); pp. 179-186; Apr. 1998.
Methot; Get the picture with a gps for smile design in 3 steps; Spectrum; 5(4); pp. 100-105; (year of pub. sufficiently earlier than effective US filing date and any foreign priority date) 2006.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Patterson Dental; Cosmetic imaging; 2 pages retrieved from the internet (http://patterson.eaglesoft.net/cnt_di_cosimg.html) on Jun. 6, 2008.
Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.
Sarment et al.; Accuracy of implant placement with a sterolithographic surgical guide; journal of Oral and Maxillofacial Implants; 118(4); pp. 571-577; Jul. 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-Vision_The smile-vision cosmetic imaging system; 2 pages; retrieved from the internet (http://www.smile-vision.net/cos_imaging.php) on Jun. 6, 2008.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
Vevin et al.; Pose estimation of teeth through crown-shape matching; In Medical Imaging: Image Processing of International Society of Optics and Photonics; vol. 4684; pp. 955-965; May 9, 2002.
Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.
Wiedmann; According to the laws of harmony to find the right tooth shape with assistance of the computer; Digital Dental News; 2nd vol.; pp. 0005-0008; (English Version Included); Apr. 2008.
Wong et al.; Computer-aided design/computer-aided manufacturing surgical guidance for placement of dental implants: Case report; Implant Dentistry; 16(2); pp. 123-130; Sep. 2007.
Wong et al.; The uses of orthodontic study models in diagnosis and treatment planning; Hong Knog Dental Journal; 3(2); pp. 107-115; Dec. 2006.
Yaltara Software; Visual planner; 1 page; retrieved from the internet (http://yaltara.com/vp/) on Jun. 6, 2008.
Zhang et al.; Visual speech features extraction for improved speech recognition; 2002 IEEE International conference on Acoustics, Speech and Signal Processing; vol. 2; 4 pages; May 13-17, 2002.
Arnone et al.; U.S. Appl. No. 16/235,449 entitled "Method and system for providing indexing and cataloguing of orthodontic related treatment profiles and options," filed Dec. 28, 2018.
Mason et al.; U.S. Appl. No. 16/374,648 entitled "Dental condition evaluation and treatment," filed Apr. 3, 2019.
Brandt et al.; U.S. Appl. No. 16/235,490 entitled "Dental wire attachment," filed Dec. 28, 2018.
Kou; U.S. Appl. No. 16/270,891 entitled "Personal data file," filed Feb. 8, 2019.

ADJUSTMENT OF TOOTH POSITION IN A VIRTUAL DENTAL MODEL

RELATED APPLICATIONS

This application is a divisional of U.S. application Ser. No. 13/477,879, filed May 22, 2012, the entire contents of which are hereby incorporated by reference.

BACKGROUND

The present disclosure is related generally to the field of dental treatment. More particularly, the present disclosure is related to methods, devices, and systems for adjustment of tooth position in a virtual dental model.

Dental treatments may involve repositioning misaligned teeth and changing bite configurations for improved cosmetic appearance and dental function. Orthodontic repositioning can be accomplished, for example, by applying controlled forces to one or more teeth over a period of time.

As an example, orthodontic repositioning may be provided through a dental process that uses positioning appliances for realigning teeth. Such appliances may utilize a thin shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement.

Such systems typically utilize materials that are light weight and/or transparent to provide as a set of appliances that can be used serially such that as the teeth move, a new appliance can be implemented to further move the teeth.

With computing device-aided teeth treatment systems, an initial digital data set (IDDS) representing an initial tooth arrangement may be obtained. The IDDS may be obtained in a variety of ways.

For example, the patient's teeth may be imaged to obtain digital data using direct and/or indirect structured light, X-rays, three-dimensional X-rays, lasers, destructive scanning, computing device-aided tomographic images or data sets, magnetic resonance images, intra-oral scanning technology, photographic reconstruction, and/or other imaging techniques. The IDDS can include an entire mouth tooth arrangement, some, but not all teeth in the mouth, and/or it can include a single tooth.

A positive model and/or negative impression of the patient's teeth or a tooth may be scanned using an X-ray, laser scanner, destructive scanner, structured light, and/or other range acquisition system to produce the IDDS. The data set produced by the range acquisition system may be converted to other formats to be compatible with the software which is used for manipulating images within the data set, as described herein.

After scanning, a virtual dental model including teeth of an upper jaw and a lower jaw may be generated. However, the upper jaw and lower jaws of the virtual dental model may not be aligned with respect to each other. Thus, a bite setting operation may be performed to align the virtual dental model including the upper and lower jaws. Other operations may be performed to reposition the teeth within the virtual dental model to a desired final position representing a desired final position for the physical teeth of the patient.

DETAILED DESCRIPTION

Figure 1:
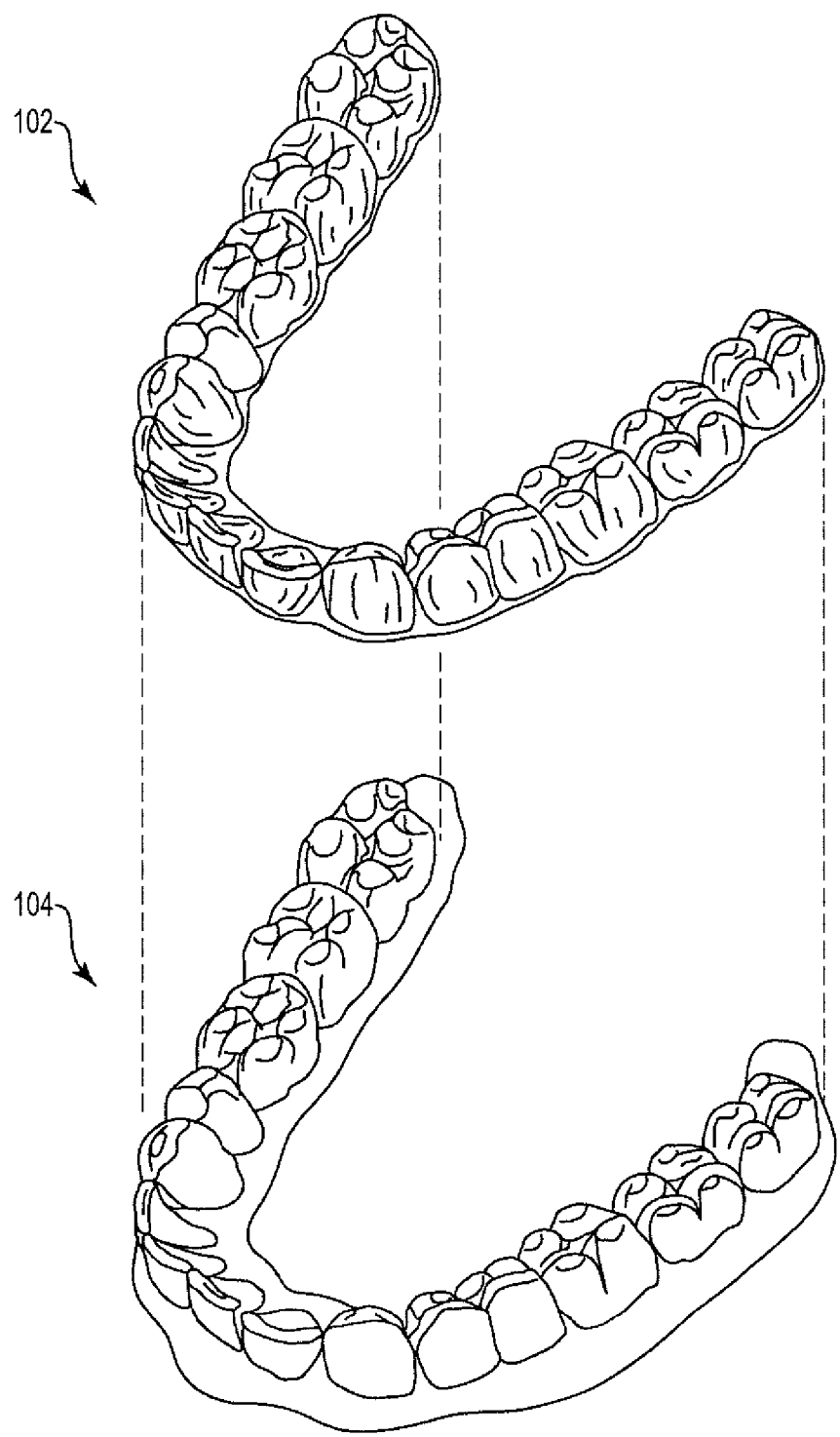
FIG. 1 illustrates a dental position adjustment appliance being applied to a set of teeth according to one or more embodiments of the present disclosure.

Setting up a final position of teeth in a virtual dental model includes a number of steps, some of which have previously included the use of human input (e.g., through the use of a computing device) to improve a quality of the final position that may be generated by a computing device. For example, one previous approach included constructing a desired archform for the virtual dental model, snapping the teeth of the virtual dental model to the desired archform, and then manually adjusting the teeth to improve occlusion between the upper and lower jaws of the virtual dental model. Manual adjustment may introduce errors and/or inefficiencies into the process that could be remediated by an automatic (e.g., fully automatic) final position setup. However, there is no straightforward mechanism to automate the manual adjustment process that may be based on human intuition or user preference rather than a formulaic approach.

Setting up a final position can include resolving a number of considerations for the final position such as teeth alignment within an arch, occlusion of anterior and posterior teeth, correcting overbite and/or overjet, etc. A number of embodiments of the present disclosure can provide an automatic final position setup with minimal manual adjustment for a virtual dental model. Minimal manual adjustment can include simple manual adjustment functions to fine tune an "ideal" result for the final position setup rather than manual inputs of a number of features, such as archform adjustment, symmetry occlusal archform, local tooth position, interproximal reduction (IPR), anterior and posterior occlusion, biting simulation, among other features. One or more embodiments of the present disclosure can include automatic IPR design, fast crowding computation, fast collision depth detection, anterior and/or posterior occlusion measurement, and/or biting simulation, among other features.

In general, a goal of orthodontic treatment can be to correct malocclusions such as crooked teeth, spacing (e.g., gaps between teeth), crowding (e.g., overlapping teeth), deep-bite (e.g., upper anterior teeth being too low), open bite (e.g., a gap between upper and lower jaws in the anterior section), and/or cross bite (e.g., an upper tooth behind a lower tooth), among others.

The present disclosure provides computing device implemented methods, computing device readable media, and systems for adjustment of tooth position in a virtual dental model. Virtual dental modeling can include detecting space and/or collision between a number of posterior teeth of an upper jaw and a number of posterior teeth of a lower jaw in a virtual dental model that has been set in a preliminary target position. An energy function can be defined including the space and/or collision, tooth root movement, and align points. Weights can be assigned for each variable in the energy function. A position of the number of posterior teeth of the upper jaw and the number of posterior teeth of the lower jaw can be adjusted in six degrees of freedom to minimize the energy function. The detection, definition, assignment, and adjustment can be repeated until the energy function converges. The weights can be adjusted to reduce the space and/or collision.

Feature points, such as cusps and grooves, can be automatically calculated for teeth (e.g., posterior teeth) of jaws in a virtual dental model. For example, a cusp point can be a subset of local maximum extremes of points in the data comprising a particular tooth and groove points can be calculated as a subset of local minimum extremes of the data comprising the particular tooth. Between an upper and lower jaw, for good occlusion, the cusps and grooves should correspond to each other as described in more detail below.

Based on the feature points, for each jaw in the virtual dental model, feature splines can be calculated (e.g., labial cusp feature splines, lingual cusp feature splines, groove features splines, etc.). The feature splines calculated based on a current position of the teeth in the virtual dental model can be referred to as current feature splines, while feature splines calculated based on a target dentition can be referred to as target feature splines. The target feature splines can be calculated based on interaction between respective feature splines of both jaws (e.g., where the lingual cusps feature spline of the upper jaw corresponds to the groove feature spline of the lower jaw).

An attractive force can be modeled between a feature point on one of the number of current feature splines and a corresponding feature point on a corresponding one of the number of target feature splines. The corresponding feature point on the target feature spline can be the feature point from the current feature spline projected to the target feature spline. The modeled attractive force can encourage the feature point to move from its current position to its target position.

A repulsive (e.g., collision) force can be modeled for collisions between a point in upper jaw and a point in the lower jaw. A collision in the virtual dental model can be represented as a set of collision spots, where each spot is connected to a component of intersection between shapes of two different teeth. A mass center, normal, and depth can be calculated for each collision spot. The repulsive force can be implemented for pairs of collision points such that a particular collision spot is pushed along a normal where the tooth movement is equal to half of the depth, for example.

A stabilization force can be modeled to limit motion of a tooth to be within a range of motion within one of the upper jaw and the lower jaw. Stabilization forces can be implemented as pairs of points for matching, however the points are matched to themselves (e.g., to discourage tooth movement in the virtual dental model). For example, a tooth root can be used as a stabilization point. In some embodiments, anisotropic matching constraints can be applied to the pairs of points (e.g., penalties during matching that are differently controlled for tooth rotation and translation degrees of freedom). Using anisotropic penalties for rotation can allow for selective control and suppress undesired tooth rotation such as angulation and/or angular rotation. Using anisotropic penalties for translation can allow for selective control and suppress undesired tooth translation such as mesial/distal shifts and/or extrusion/intrusion.

Combining the attractive forces, repulsive forces, and stabilization forces in the virtual dental model can allow for incremental construction of a target position during an iterative process with relatively few steps. However, some embodiments may exclude the use of collision forces in the calculation of the target position and may resolve possible inter-jaw tooth collisions from the current position without using the attractive forces.

On each step, for example, the forces can be recalculated. The forces can be weighted, and the weights can be adjusted so that tooth movement within a particular step (e.g., defined treatment step as described herein) is within a specified tolerance (e.g., for patient comfort, etc.). The sequence of such steps can provide the tooth movement trajectory from the current position to the target position as part of a treatment plan. Additional details of biting simulation and force modeling are described below with respect to FIG. 8.

FIG. 1 illustrates a dental position adjustment appliance being applied to a set of teeth according to one or more embodiments of the present disclosure. Appliances according to the present disclosure can include, in some embodiments, a plurality of incremental dental position adjustment appliances. The appliances, such as appliance 102 illustrated in FIG. 1, can be utilized to affect incremental repositioning of individual teeth in the jaw, among other suitable uses. Appliances, such as appliance 102, can be fabricated according to a virtual dental model that has had positions of a number of teeth adjusted according to one or more embodiments of the present disclosure.

Appliances can include any positioners, retainers, and/or other removable appliances for finishing and maintaining teeth positioning in connection with a dental treatment. These appliances may be utilized by the treatment professional in performing a treatment plan. For example, a treatment plan can include the use of a set of appliances, created according to models described herein.

An appliance (e.g., appliance 102 in FIG. 1) can, for example, be fabricated from a polymeric shell, and/or formed from other material, having a cavity shaped to receive and apply force to reposition one or more teeth from one teeth arrangement to a successive teeth arrangement. The shell may be designed to fit over a number of, or in many instances all, teeth 104 present in the upper and/or lower jaw.

Figure 2:
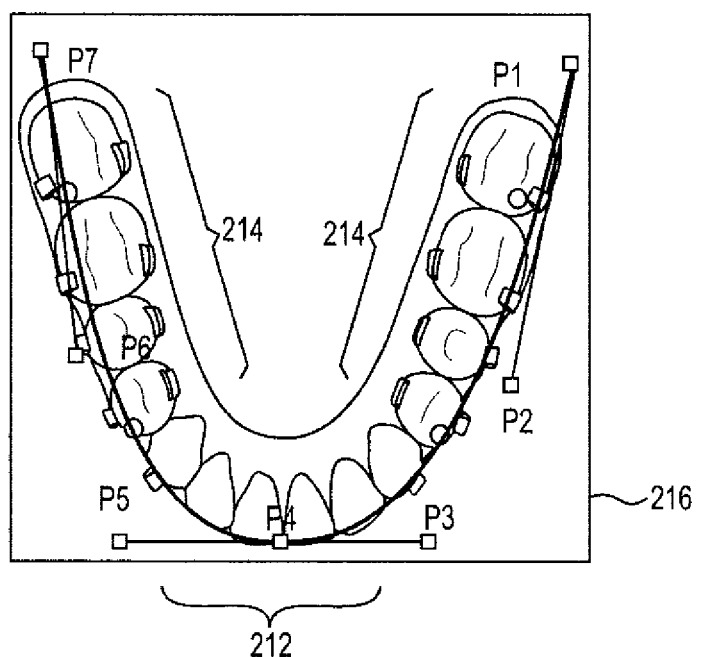
FIG. 2 illustrates a virtual archform according to one or more embodiments of the present disclosure.

FIG. 2 illustrates a virtual archform 216 according to one or more embodiments of the present disclosure. In general, an archform 216 can be a smooth curve that passes through feature points in the teeth in a dental arch. The archform 216 can serve as a baseline for alignment of the teeth. One dental arch can have multiple archforms based on the feature points used to determine the archform (e.g., a contact point archform, a facial axis archform, an occlusal archform, etc.). For example, an occlusal archform can pass through occlusion points of the upper and lower jaws, where for the lower jaw, the archform passes through the buccal ridges of posterior teeth 214 and incisal ridges of anterior teeth 212, and where for the upper jaw, the archform can pass through the central groove of molar and premolar and the contact points of the anterior teeth 212. For a desired final position setup, the occlusal archforms for the upper and lower jaw can match with each other such that teeth in the virtual dental model can move freely along the occlusal archform to solve space and/or crowding problems while maintaining anterior and posterior occlusion.

In general, the archform 216 can be a smooth three-dimensional (3D) curve such that it can control both horizontal and vertical tooth movement. The archform 216 can have anterior symmetry such that the anterior teeth 212 are symmetric on opposite sides of the jaw. The archform 216 can be adjustable in size and shape. The example illustrated in FIG. 2 includes a number of control points (e.g., $P_1$, $P_2$, $P_3$, $P_4$, $P_5$, $P_6$, and $P_7$) to control the shape and position of the archform 216.

In some embodiments, the archform 216 can be formed from a number of segments of a cubic spline curve. Examples of such splines include a labial cusps feature spline (e.g., a spline formed based on cusps on the labial side of the teeth), a lingual cusps feature spline (e.g., a spline formed based on cusps on the lingual side of the teeth), and a grooves feature spline (e.g., a spline formed based on the grooves in the teeth), among others.

An occlusal archform can be created from occlusal points in a jaw. An occlusal point can be detected for each tooth based on tooth type. For a lower incisor, the occlusal point can be detected by finding a facial plane that best fits the buccal vertices of the incisor, detecting the ridge vertices that are highest points in a direction from root-to-ridge of the incisor for different directions along the ridge, project ridge vertices into the facial plane, use a line to best fit the projected ridge vertices (e.g., the ridge line of the tooth), detect the tip point (e.g., the highest vertex near the facial axis point), and project the top point to the ridge line as the occlusal point.

For upper central incisors, the occlusal point can be detected and shifted in the buccal direction for a first distance (e.g., 1.0 mm) and in a direction from ridge-to-root for a second distance (e.g., 2.5 mm). The first and second distances can be determined according to a desired overbite and overjet distance. For an upper lateral incisor, the occlusal point can be shifted a third distance (e.g., 2.0 mm) in a direction from ridge-to-root. Selecting a third distance less than the second distance can make lateral incisor leveling higher than the central incisors.

For a lower premolar and/or canine, the occlusal point can be detected by constructing a middle plane, which can be a plane extending in a direction from root-to-tip and from facial-to-lingual portions of the tooth, finding a vertex that's near the middle plane and in the buccal side of the tooth, then projecting the vertex into the middle plane as a facial middle vertex, using a line to best fit all facial middle vertices, and projecting the tip point into the facial middle line to get the occlusal point.

For an upper canine, the occlusal point can be shifted a first distance (e.g., 1.5 mm) in a facial-lingual direction and a second distance (e.g., 3.0 mm) in a tip-root direction. When the second distance from he upper canine is greater than the second distance for the central incisor, the tip of the upper incisor can be lower than the central incisor.

For an upper premolar and molar, the occlusal point can be the center of the crown surface. For example, the center of the crown surface can be the point where a central axis, in a root-tip direction, passes through the tooth crown occlusal surface.

An occlusal plane for each jaw in the virtual dental model can be created. A normal of an occlusal plane can be defined as a Z-direction of an arch coordinate system. Crown centers can be projected into the occlusal plane. Middle points of paired crown centers (e.g., crown centers of left and right second molars) can be computed. A line that is best fit to the middle points can be defined as the Y-axis. The X-axis can be defined as the line that passes the crown center of the second molars.

A first initial archform (e.g., an initial lower archform) can be constructed from initial teeth positions by best fitting the archform to feature points. A second initial archform (e.g., an initial upper archform) can be constructed based on the first initial archform (e.g., by enlarging the anterior, such as by moving the control points $P_1$ and $P_7$ to make the archform wider and/or by adding extended occlusal points to extend the archform posterior in the direction of the posterior occlusal points and enable teeth distalization in the archform).

To help keep the archform smooth and the anterior teeth symmetric, the following constraints can be applied to the control points: $P_4 \cdot x = 0$, $P_3 \cdot x = -P_5 \cdot x$ (to make the anterior symmetric to the middle of the arch); $P_3 \cdot y = P_4 \cdot y = P_5 \cdot y$ (to keep the anterior perpendicular to the middle of the arch); and $P_3 \cdot z = P_4 \cdot z = P_5 \cdot z$ (to keep the anterior flat). Then, the three anterior control points $P_3$, $P_4$, and $P_5$, are $P_3 = (-w, l, h)$, $P_4 = (0, l, h)$, $P_5 = (w, l, h)$, where "w" is the anterior width, "l" is the arch length, and "h" is the anterior height. Therefore, the seven control points can be reduced to five control points ($P_1$, $P_2$, $P_6$, $P_7$, Q), where $Q = (w, l, h)$.

Points used to estimate the archform are referred to herein as $Q_1, Q_2, \ldots, Q_n$, where $Q_1$ and $Q_n$ are extended occlusal points and the others are occlusal points. A spline curve can be best fit by computing the distance of one point to a next point as $l_i$, $i = 1, 2, \ldots (n-1)$ and the length of two segments as $$l_a = \sum_{i=1}^{m-2} l_i + \frac{l_{m-1}}{2},$$

$$l_b = \sum_{i=m}^{n-1} l_i + \frac{l_{m-1}}{2},$$

where m−1 and m are the two center points in the curve. The parameter of the point $Q_i$ can be computed as $$u_i = u_{i-1} + \frac{l_i}{l_a},$$

if $Q_i$ is in the first segment and $$u_i = u_{i-1} + \frac{l_i}{l_b},$$

if $Q_i$ is in the second segment. The least square function $$J = \sum_{i=1}^{n} \|P(u_i) - Q_i\|^2$$

can be solved, where $P(u_i)$ is a point in the spline curve with control points $P_1$, $P_2$, $P_6$, $P_7$, $Q$ and parameter $u_i$, as:

$t=u$ $P=(1-t)^3 P_1 + 3*t(1-t)^2 P_2 + 3*t^2(1-t) P_3 + t^3 P_4$ if it is in the first section, and as:

$t=u-1$ $P=(1-t)^3 P_4 + 3*t(1-t)^2 P_5 + 3*t^2(1-t) P_6 + t^3 P_7$ if it is in the second section, where $P_3$, $P_4$, $P_5$ is the linear function of $Q$.

The upper archform can be constructed from the lower archform. The posterior of the upper archform can be set equal to the posterior of the lower archform. The anterior difference can be defined as $w_d$, $l_d$, $h_d$ in the X,Y,Z direction. The upper control points can be defined as:

$P_2^u = P_2^1 + [0.8*w_d \; 0 \; -1.2*h_d]^T$ $P_3^u = P_3^1 + [-w_d \; l_d \; h_d]^T$ $P_4^u = P_4^1 + [0 \; l_d \; h_d]^T$ $P_5^u = P_5^1 + [w_d \; l_d \; k_d]^T$ $P_6^u = P_6^1 + [-0.8*w_d \; 0 \; -1.2*h_d]^T$

The anterior difference values $w_d$, $l_d$, $h_d$ can be adjusted to change the anterior occlusion (e.g., overjet, overbite).

Some examples of orthodontic arch adjustments include anterior expansion/contraction, arch shape change (e.g., from a "U" shape to a "V" shape), leveling of the anterior (e.g., changing the Spee curve), and/or posterior expansion (e.g., left and/or right), among others.

As an example, a desired change of an archform can include anterior expansion E, anterior left movement $M_l$, anterior right movement $M_r$, and anterior leveling L. The control points can be changed as:

$$P_2 \mathrel{+}= \begin{bmatrix} 0.6*M_l \\ 0 \\ -1.2*L \end{bmatrix}$$

$$P_3 \mathrel{+}= \begin{bmatrix} -0.4*E - 1.0*M_l \\ 0.6*E \\ 1.0*L \end{bmatrix}$$

$$P_4 \mathrel{+}= \begin{bmatrix} 0.0 \\ 0.6*E \\ 1.0*L \end{bmatrix}$$

$$P_5 \mathrel{+}= \begin{bmatrix} 0.4*E + 1.0*M_r \\ 0.6*E \\ 1.0*L \end{bmatrix}$$

$$P_6 \mathrel{+}= \begin{bmatrix} 0.6*M_r \\ 0 \\ -1.2*L \end{bmatrix}$$

Figure 3:
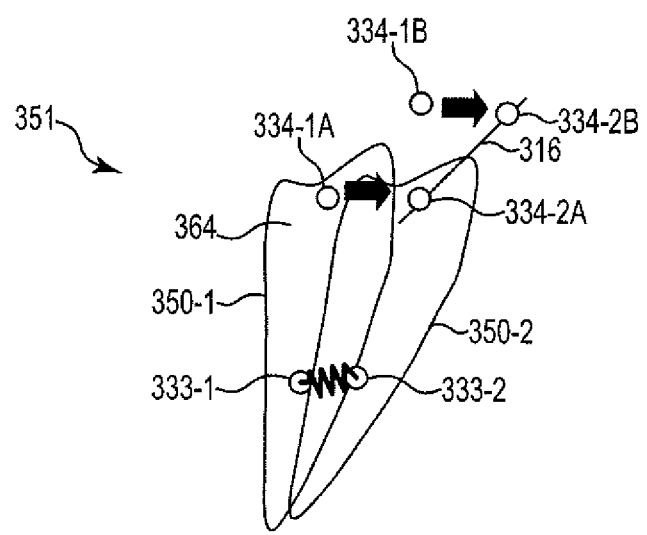
FIG. 3 illustrates a virtual dental model of a tooth with a number of align points and an archform according to one or more embodiments of the present disclosure.

FIG. 3 illustrates a virtual dental model 351 of a tooth 364 with a number of align points 334-1A, 334-1B, 334-2A, 334-2B and an archform 316 according to one or more embodiments of the present disclosure. The virtual dental model 351 includes the tooth 364 in a first position 350-1 with align points 334-1A and 334-1B and in a second position 350-2 with corresponding align points 334-2A and 334-2B. The align points are generally referred to as align points 334.

Because the tooth 364 is a 3D object, alignment of only the occlusal point, as described herein, cannot guarantee alignment of the tooth 364 as a whole. As such, two align points 334 can be used for each tooth 364 to align to the archform 316 and a third point (e.g., a root center) can be used to define the transformation for the tooth 364. The tooth 364 in the first position 350-1 includes root center 333-1 and the tooth 364 in the second position 350-2 includes corresponding root center 333-2. The root center is generally referred to as root center 333.

For example, two align points 334 can be created for the tooth 364 (e.g., one on the mesial side of the occlusal point and one on the distal side of the occlusal point). As described herein, the align points 334 can be based on the occlusal point and the facial axis basis of the tooth 364. The facial axis basis can be defined as the basis (e.g., coordinate system) near the facial axis point using the facial axis point as the origin. The X-axis can be defined as the normal direction near the facial axis point. The Z-axis can be defined as the facial axis of clinical crown (FACC) direction. The align points can be defined within a particular distance (e.g., 2 mm) of the occlusal point in a direction along the Y-axis, perpendicular to the FACC line.

Align points 334-1A and 334-1B for the tooth 364 can be moved to the archform 316. Two align points 334-2A and 334-2B in the archform 316 are based on the archform basis. For any point in the archform 316, the origin of the archform basis is the point itself. The Z-axis can be defined as the occlusal plane norm. The X-axis can be perpendicular to the Z-axis and to a tangent of the archform 316. The align points 334-1B and 334-2B in the archform 316, then, are defined in a Y-axis (e.g., within 2 mm from the origin of the archform basis). The archform align points 334-1B and 334-2B can be computed by getting the crown center of the tooth 364, finding the closest point in the archform 316, constructing the arch basis in the archform 316 in the closest point, and computing the respective archform align point.

To move the tooth 364 from the first position 350-1 to the second position 350-2 corresponding to the archform 316, the occlusal point, the align points 334, and the root center 333 can be used to compute the transformation (R,T), which can be based on optimization of the object function of each point's movement:

$$J = \sum_{i=1}^{N} \|w_i(RP_i + T - Q_i)\|^2,$$

where $P_i$ is the first position 350-1, $Q_i$ is the second position 350-2, and $w_i$ is the weight of the movement. Larger weights can force $P_i$ and $Q_i$ to be closer.

In some embodiments, the align points 334-1A and 334-1B can be moved to the archform 316 and the root center 333 can be kept close to its first position 333-1 while the weight of movement for the root center 333 is set relatively low (e.g., 0.1~0.2) such that it can be moved more freely to promote accurate alignment of the align points 334 to the archform 316. Then, the root center 333 can be pulled to the same level of the first position 333-1, while the weight of movement of the root center 333 is increased (e.g., 0.5~5.0) depending on the type of tooth 364, where a larger weight is used for teeth that are not desired to have much intrusion and/or extrusion, such as molars.

However, even after alignment with the archform 316, additional adjustment of the tooth 364 may still be desired. For example, tooth angulation may be set within a normal range based on a doctor's prescription or protocol, upper lateral incisors may be leveled, and/or a tooth 364 may be manually adjusted to improve alignment, among others. To provide for such adjustment, the align points 334 in the archform 316 can be adjusted to change a relative position of the tooth 364. Such changes can be performed manually and/or automatically.

Figure 4:
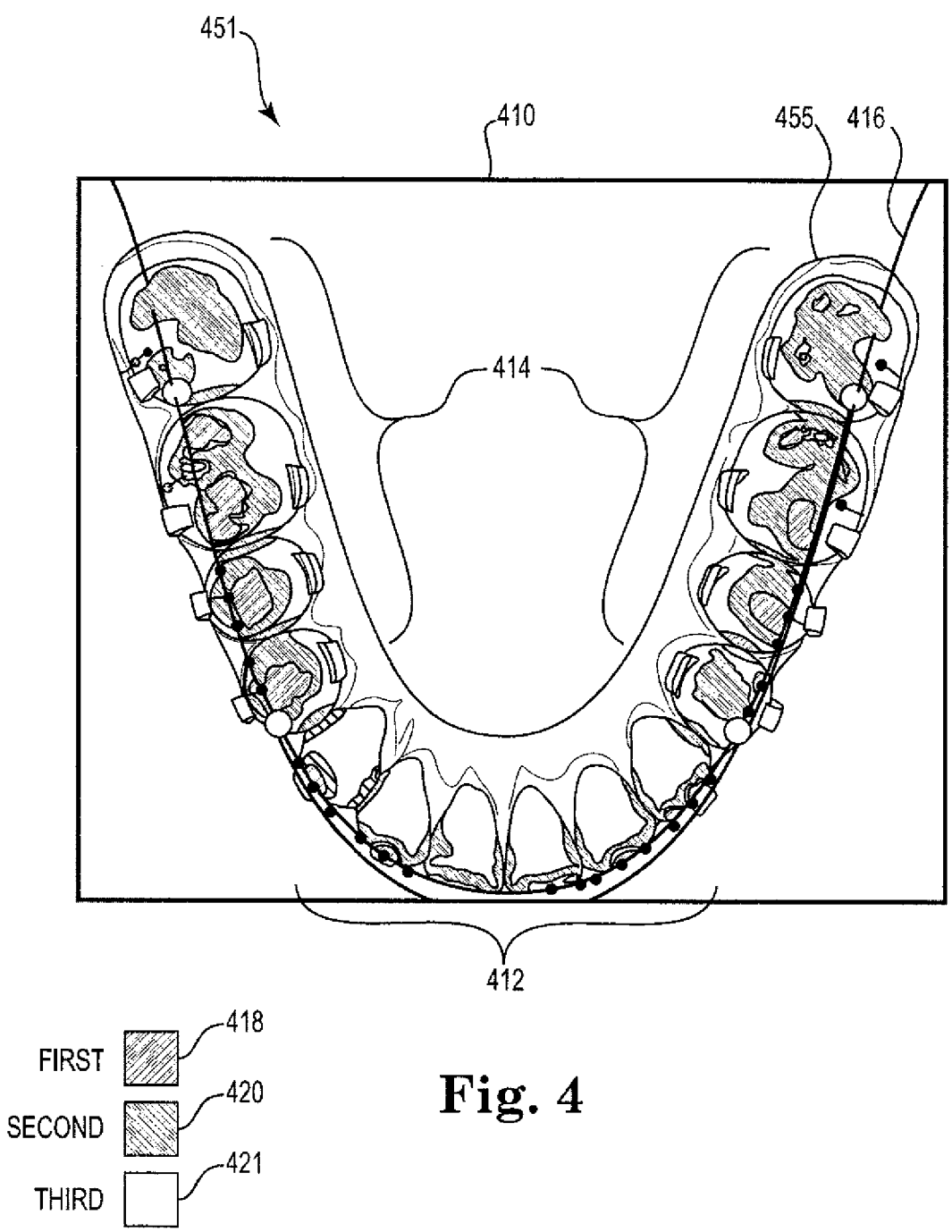
FIG. 4 illustrates an occlusogram of a virtual dental model of a jaw according to one or more embodiments of the present disclosure.

FIG. 4 illustrates an occlusogram 410 of a virtual dental model 451 of a jaw 455 according to one or more embodiments of the present disclosure. Treatment plans including the use of virtual dental modeling can more heavily weight alignment for occlusion of the anterior teeth 412 while more heavily weighting contact and collision for occlusion of the posterior teeth 414. Anterior teeth 412 can include incisors and canines, while posterior teeth 414 can include premolars and molars. Alignment of posterior teeth 414 into an archform 416 (e.g., according to a treatment plan) can provide a good initial corrected position for the posterior teeth 414, but contact and collision problems may remain.

To promote visualization of such contact and collision problems, an occlusogram 410 can be created. Collision and occlusal regions between teeth of an upper jaw and a lower jaw of a virtual dental model can be computed and color coded. In some instances, a collision (e.g., a collision region) can be defined as a mesh vertex from one tooth (e.g., a posterior tooth) of one of an upper jaw and a lower jaw being inside a tooth from the opposite jaw, as described herein. An occlusal region can include a mesh vertex from one tooth (e.g., a posterior tooth) of one of the upper jaw and the lower jaw being within a threshold distance from another tooth of the opposite jaw. A space region can include a mesh vertex from one tooth (e.g., a posterior tooth) of one of the upper jaw and the lower jaw being outside the threshold distance from the other tooth of the opposite jaw.

Figure 5:
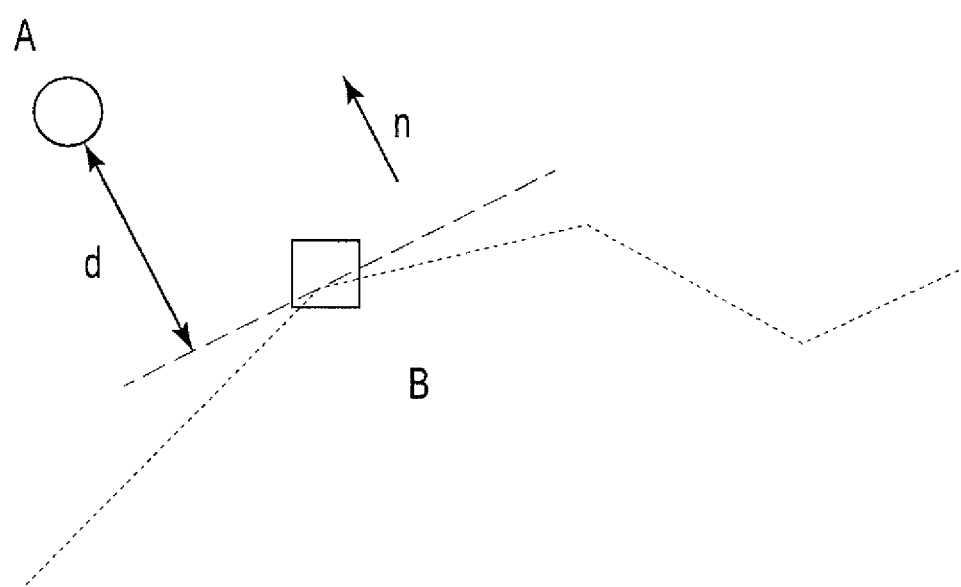
FIG. 5 is a diagram illustrating point to mesh distance according to one or more embodiments of the present disclosure.

FIG. 5 is a diagram illustrating point to mesh distance according to one or more embodiments of the present disclosure. As described herein, each tooth in a virtual dental model can be represented by a mesh (e.g., a closed mesh). Each vertex in the mesh for a particular tooth can have a normal assigned to it (e.g., an average normal of triangles linked to the vertex, where the mesh is a triangular mesh).

A distance (d) can be computed from a particular vertex point (A) to a nearest point in the mesh (B) in the direction of the normal (n) for the point A. If d<0 (or some small value such as 0.1 millimeter (mm) or −0.1 mm), A is inside the mesh and it's in a collision region. Points in collision regions can be displayed in a first color (e.g., red, as represented by first hatching 418 in FIG. 4). If $d_c$>d>0, A is outside the mesh and in an occlusal region, where $d_c$ is a control distance having a value that can be set to a distance defining a boundary between what is considered an occlusal region and a space region (e.g., 1 mm). Points in occlusal regions can be displayed in a second color (e.g., green, as represented by second hatching 420 in FIG. 4). If d>$d_c$, then A is in a space region. Points in space regions can be displayed in a third color (e.g., white, as represented by third hatching 421 in FIG. 4). In some embodiments, additional regions can be defined, such as an intermediate region between collision and occlusal regions, which can be displayed in a fourth color (e.g., yellow, not specifically illustrated in FIG. 4).

A collision region is an area that includes vertices in a mesh of a first tooth that are inside the mesh of a second tooth (e.g., a first tooth of an upper jaw and a second tooth of a lower jaw). Collisions between teeth in a virtual dental model may be undesirable because they cannot exist with physical teeth (e.g., one tooth cannot be inside of another tooth). Furthermore, collisions included in a virtual dental model representing a stage in a treatment (e.g., a final stage) may only be resolved, in some instances, by removing some enamel of a tooth, for example, by IPR.

An occlusal region is an area that includes vertices in a mesh of a first tooth that are close to vertices in a mesh of a second tooth (e.g., a first tooth of an upper jaw and a second tooth of a lower jaw). For posterior teeth, it can be desirable to maximize the occlusal region for better grind and chew functionality.

Figure 6:
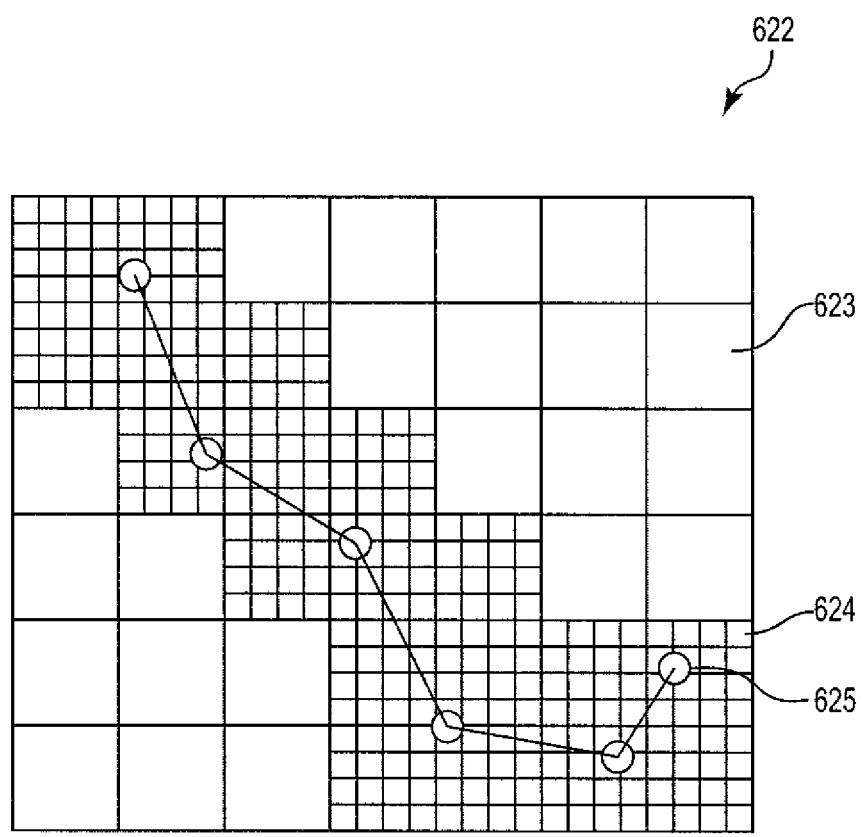
FIG. 6 illustrates a map of points in a virtual dental model according to one or more embodiments of the present disclosure.

FIG. 6 illustrates a map of points in a virtual dental model according to one or more embodiments of the present disclosure. Before a distance (d) can be computed from a particular vertex point (A) to a nearest point in the mesh (B) in the direction of the normal (n) for the point A, a determination needs to be made as to what the nearest point is. A basic idea of many nearest point searches is to organize scattered vertices in space in such a way that for each search, only a small number of comparisons is needed (e.g., rather than comparing distances between a particular point and all other points in the mesh). In contrast, one or more embodiments of the present disclosure can store the closest vertex for each point in the neighborhood of the model. Given a particular 3D point, a closest vertex can then immediately be found. In order to reduce an amount of memory used with such embodiments, a coarse to fine approach can be used.

First, a bounding box 622 that is at least bigger than a tight bounding box of a number of vertices in the model can be found. The bounding box can be divided (e.g., uniformly divided) into many rectangles (boxes in 3D) called coarse boxes (e.g., coarse box 623). However, when a particular box is near a vertex in the model, it can be subdivided into even smaller boxes (e.g., fine boxes, such as fine box 624). For each box, the closest vertex to the center of the box can be stored (e.g., such as vertex 625).

For points other than box centers, there may be an error in the distance to the closest vertex of the mesh since every box stores only the closest vertex to its center. However, the coarse box is far from the model, so the error is small compared to the distance to the vertex. For the fine box, its size is small enough so that the error is also small compared to the distance. This tradeoff between accuracy and the amount of data stored can be beneficial to promote fast searches for a closest mesh vertex pair.

In some embodiments, determining a plurality of closest mesh vertex pairs can include bounding a virtual dental model with a first box and dividing the first box into a plurality of coarse boxes. Those of the plurality of coarse boxes that are near a mesh vertex can be subdivided into a plurality of fine boxes. A closest mesh vertex can be stored for each of the plurality of coarse boxes and each of the plurality of fine boxes. By reference to the stored closest mesh vertex, the plurality of closest mesh vertex pairs for a posterior tooth of the upper jaw and the corresponding posterior tooth of the lower jaw can be determined.

In various embodiments, determining a plurality of closest mesh vertex pairs can include bounding a virtual dental model with a first box and dividing the first box into a plurality of coarse boxes. A set of neighboring coarse boxes for a particular mesh vertex can be found and the particular mesh vertex can be stored as a closest mesh vertex for those of the neighboring coarse boxes that do not have a stored closest mesh vertex. The set of neighboring coarse boxes can be subdivided into a plurality of fine boxes. The particular mesh vertex can be stored as a closest mesh vertex for those of the plurality of fine boxes that were subdivided from coarse boxes having a stored closest mesh vertex that is the particular mesh vertex. By reference to the stored closest mesh vertex, the plurality of closest mesh vertex pairs for a posterior tooth of the upper jaw and the corresponding posterior tooth of the lower jaw can be determined.

In a number of embodiments, determining a plurality of closest mesh vertex pairs can include bounding a virtual dental model with a first box, dividing the first box into a plurality of coarse boxes, and, for a particular vertex, setting a reference to a closest vertex as null. For each vertex in the model, neighboring coarse boxes can be found. For those coarse boxes having no reference to a closest vertex (e.g., null), the reference can be set to the current vertex, otherwise the new closest vertex to the box can be found. The coarse boxes closest to the particular vertex can be subdivided into fine boxes and the fine boxes can be filled with references to a new closest vertex.

Thus, according to a number of embodiments of the present disclosure, determining a plurality of closest mesh vertex pairs can be achieved by making only a small number of comparisons (e.g., as opposed to comparing all or most vertices in a model). Using a k-dimensional tree (k-d tree) as a space partitioning data structure for organizing points in k-dimensional space and/or an octree (e.g., a tree data structure in which each internal node has eight children) may be relatively fast alternative approaches for a closest mesh vertex pair search. However, the relatively processing-intensive requirements of computation of collision and occlusion in the virtual dental models of the present disclosure make an even less processing-intensive (e.g., faster) approach to closest mesh vertex pair search, such as those described herein, advantageous.

Figure 7:
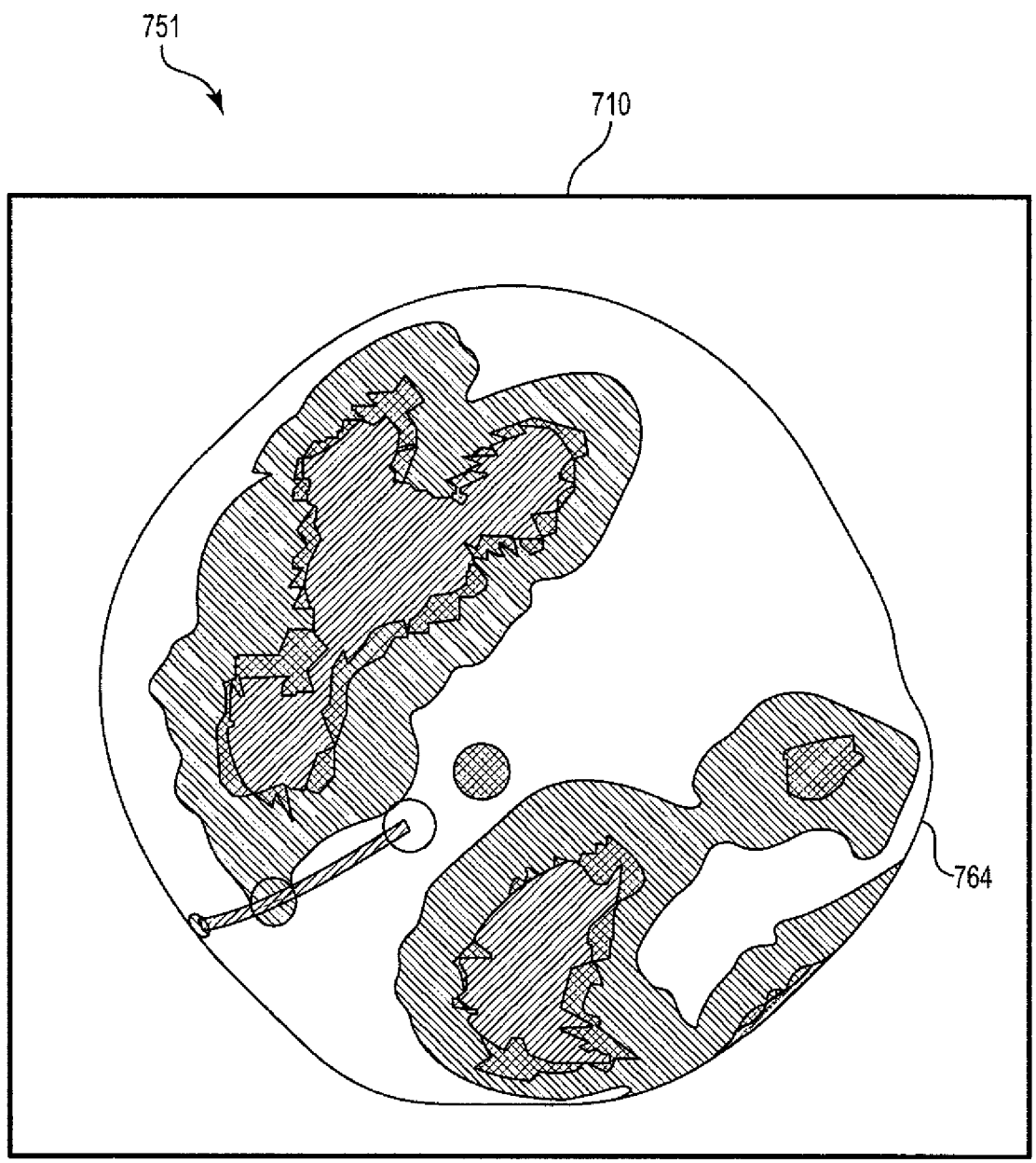
FIG. 7 illustrates an occlusogram of a virtual dental model of a tooth according to one or more embodiments of the present disclosure.
Figure 7:
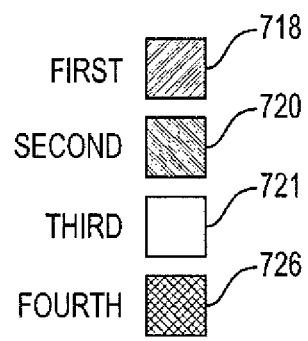

FIG. 7 illustrates an occlusogram 710 of a virtual dental model 751 of a tooth 764 according to one or more embodiments of the present disclosure. Once the point-mesh distance has been determined, such distances can be color coded for display to a user as described herein. For example, for a vertex with distance d, the color can be defined as: $d \leq -0.1$ mm, color=first color (e.g., red, as indicated by first hatching 718); $0.1$ mm$<d \leq 0.1$ mm, color=fourth color (e.g., yellow, as indicated by fourth hatching 726); $0.1$ mm$<d \leq 1$ mm, color=second color (e.g., green, as indicated by second hatching 720); $d>1$ mm, color=third color (e.g., white, as indicated by third hatching 721).

Figure 8:
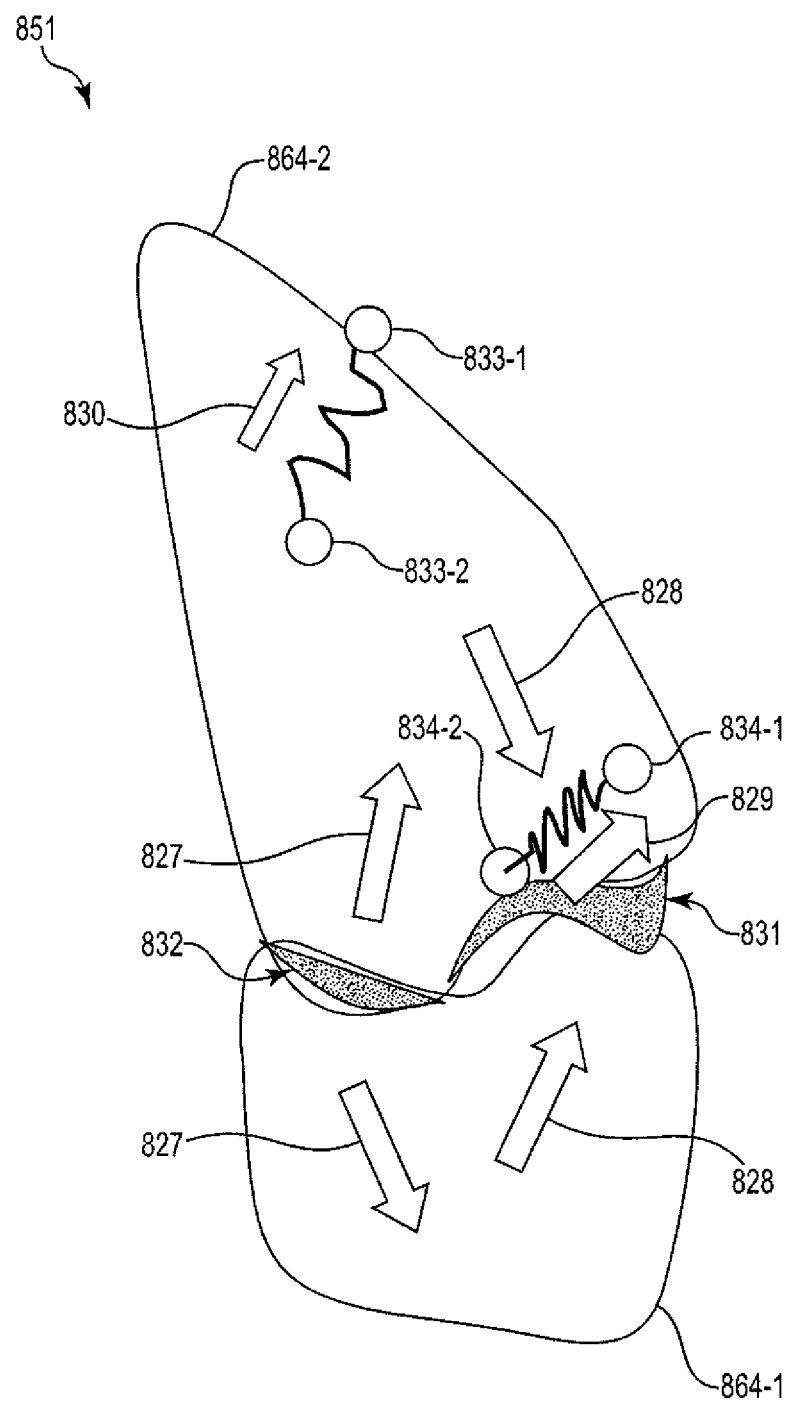
FIG. 8 illustrates a virtual dental model including two teeth with a number of forces acting thereon during a biting simulation according to one or more embodiments of the present disclosure.

FIG. 8 illustrates a virtual dental model 851 including two teeth 864-1, 864-2 with a number of forces acting thereon during a biting simulation according to one or more embodiments of the present disclosure. According to a number of embodiments of the present disclosure, a biting simulation can be used to improve posterior occlusion. An analogy can be drawn between the biting simulation and a force model such that a tooth can be moved (e.g., translated and/or rotated) by the forces created by a collision, space, and/or other reasons. While a force model is described herein to illustrate various features of the present disclosure and to promote understanding, some embodiments of the present disclosure perform a biting simulation without modeling forces (e.g., the biting simulation is implemented by directly optimizing an energy function that evaluates the collision, space, root movement, and/or alignments, as described herein).

A biting simulation can include simulating how a first jaw and a second jaw (e.g., an upper and lower jaw) of a virtual dental model fit together in respective orientations that model how physical teeth of a patient's jaws would fit together in a bite position. The biting simulation can be performed between two jaws of a virtual dental model collectively (e.g., such that the simulation is performed in consideration of all of the teeth of the virtual dental model substantially simultaneously), or individually between corresponding teeth in a first jaw and a second jaw of the virtual dental model (e.g., such that the simulation is performed successively for a corresponding tooth of a first jaw and a corresponding tooth of a second jaw until the simulation has been performed for a sufficient amount of the teeth in the jaws to return a result with a desired amount of certainty and/or accuracy, etc.). Goals of a biting simulation can include resolving collisions between corresponding teeth of the upper and lower jaws, closing posterior space between corresponding teeth of the upper and lower jaws, and/or achieving a better ridge-groove relationship between teeth of the upper and lower jaws (e.g., so that ridges of teeth of a first jaw fit nicely into the groove between teeth of a second jaw), among others.

Some examples of forces that can be applied to a number of teeth in the virtual dental model 851 during the biting simulation include collision 827, space 828, alignment 829, and root 830, among others. If there is a collision 832 between one vertex of a first tooth 864-1 and a second tooth 864-2 (e.g., a vertex in a lower tooth with a corresponding upper tooth), an amount of force 827 (e.g., a relatively small amount of force) can be created to push the first tooth 864-1 and the second tooth 864-2 apart. In some embodiments, the teeth of the virtual dental model 851 can be "hard" such that any force of collision 827 would have a greater magnitude than the other forces. However, during the biting simulation, the hardness of the teeth can be variable to help achieve a better occlusion. For example, at the beginning of the biting simulation, the collision force 827 can be set to a relatively small magnitude so that the tooth is modeled as being "soft" like a rubber that can be compressed to help promote a greater contact region between teeth in the virtual dental model. As the biting simulation progresses, the hardness of the teeth can be increased to result in an increased repulsive force of collision 827 to help remove collisions 832 between teeth of the first and the second jaw in the virtual dental model 851. In some embodiments, the hardness of the teeth (e.g., posterior teeth) can be increased according to a number of iterations of the biting simulation, can be increased manually by a user, and/or can be increased according to some other metric.

If there is space 831 between a vertex of the first tooth 864-1 and the second tooth 864-2, a space force 828 can be created to pull the first tooth 864-1 and the second tooth 864-2 closer together. Align forces 829 can be created to pull an align point from its current position 834-2 to an initial position 834-1 in a treatment planned archform (e.g., archform 416 illustrated in FIG. 4) to retain the alignment of a first jaw and/or a second jaw (e.g., where a number of teeth in the virtual dental model 851 have been aligned to the treatment planned archform prior to the biting simulation). A root force 830 can be created to pull a root of a tooth 864-2 back to its initial position 833-1 from its current position 833-2 to simulate the difficulty of moving a root of a physical tooth. Other forces can include photo attraction forces, as described herein and axial forces (e.g., simulated gravity), among others.

As described herein, the biting simulation can operate according to an energy function. The optimization (e.g., minimization) of the energy function can create a stable solution for the system (e.g., the virtual dental model). In a stable solution, all "forces" can be balanced with each other.

For each posterior tooth in a first jaw, vertex pairs can be detected. For each vertex in the occlusal surface of a particular posterior tooth in the first jaw, the nearest vertex pair to the second jaw can be detected as ($C_i$, $D_i$), where $C_i$ is a point in the tooth in the first jaw and $D_i$ is a point in a corresponding tooth in the second jaw. The midpoint is $E_i = (C_i + D_i)/2$. ($C_i$, $D_i$) can be added into a vertex pair list for the tooth in the first jaw and ($E_i$, $D_i$) can be added into a vertex pair list for the corresponding tooth in the second jaw. The distance between the vertex pairs can be computed, and if it is less than zero, then the vertex can be considered to be in collision. If the distance is greater than zero, but less than $d_c$ (e.g., 1 mm), then the vertex can be considered to be in space. If the distance is greater than $d_c$, then the vertex may be disregarded for the computation of forces. After the distance determination, the current root position and initial position before biting simulation can be computed. The current align position and initial position before the biting simulation can also be computed.

The following energy function can be constructed for teeth (e.g., every tooth) in the first jaw and in the second jaw:

$$J = w_c \sum_{i=1}^{N_c} \|R * C_i + T - E_i\|^2 + w_s \sum_{i=1}^{N_s} \|R * C_i + T - E_i\|^2 +$$

$$w_r * N_p * \|R * C_r + T - E_r\|^2 + w_a * N_p * \sum_{i=1}^{N_a} \|R * C_i + T - E_i\|^2$$

Where:
$N_c$ is the number of vertices in collision;
$w_c$ is the weight of collision energy;
$N_s$ is the number of vertices in space;
$w_s$ is the weight of space energy;
$N_p = N_c + N_p$ is the number of vertices in occlusal;
$w_r$ is the weight of root movement energy;
$w_a$ is the weight of alignment (e.g., align points) movement energy; and
(R,T) is the rotation and translation of the tooth transform.

The transformation of the tooth can be directly computed by optimizing the energy function. After the tooth has moved to a new position according to the optimization of the energy function, IPR can be computed to fit the setup. The transition from "soft" to "hard" collisions, as described herein, can include changing the weight of the collision (e.g., $w_c$).

Accordingly, an algorithm for the same can include:
(1) detecting vertex pairs of collision, space, root, and alignment;
(2) setting the weight of collision as:
   a. for iterations < a first number (e.g., 10), the weight of collision is set at a first value (e.g., 30);
   b. else, if the iteration < a second number (e.g., 20), the weight is increased by the first value (e.g., 30) every iteration;
   c. the weight is then increased by a second value (e.g., 200) every iteration;

(3) minimizing the energy function to get tooth movement (R,T);
(4) setting up IPR based on the configuration; and
(5) repeating steps 1-4 until a certain number of iterations is reached.

Figure 9:
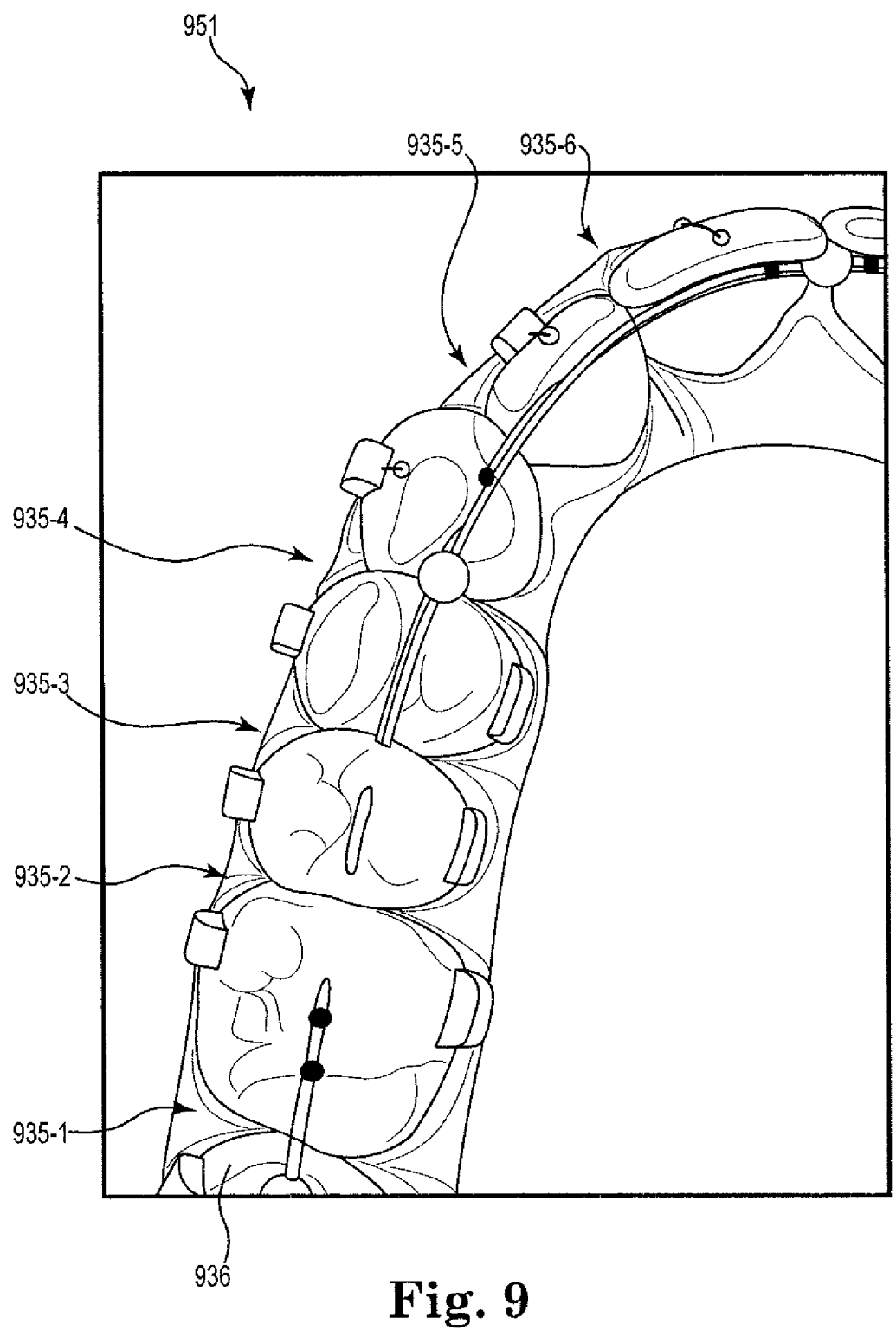
FIG. 9 illustrates a virtual dental model including crowding between teeth according to one or more embodiments of the present disclosure.

FIG. 9 illustrates a virtual dental model 951 including crowding between teeth according to one or more embodiments of the present disclosure. After teeth are aligned in an archform of a particular jaw, crowding between adjacent teeth in the jaw may be resolved by moving one or more teeth along the archform, by IPR, and/or by adjustment of the archform. According to a number of embodiments of the present disclosure, three types of teeth may be defined in a virtual dental model: non-movable, anchorage, and normal.

A tooth that has been defined as non-movable is not allowed to move. Examples of such teeth can include a pontic, a crown, a bridge, and a partially erupted tooth, among others.

A tooth that has been defined as an anchorage can be moved manually (e.g., by an operator of a user interface for the virtual dental model). Such a tooth may not automatically follow adjustments to the jaw (e.g., to the archform).

A tooth that has been defined as normal can be moved freely and may automatically follow adjustments to the jaw (e.g., to the archform). For example, anterior teeth may be defined as normal.

In some instances, there may be a physical limit to the amount of IPR that can be applied to a physical tooth. Furthermore, it may be physically easier to apply IPR to anterior teeth as opposed to posterior teeth. Considering the factors described herein, a cost function can be optimized to solve mobility, space, IPR, and/or midline considerations. Midline can refer to a middle line between two central incisors and midline shift can refer to a distance that a point on the midline shifts after the teeth have been adjusted (e.g., either physically or in the virtual dental model). The cost function can include parameters of intra-arch setup for at least one of the upper jaw and the lower jaw. For example, the cost function can be:

$$K = \sum_{i=1}^{\#} w_i z_i^2 + \sum_{i=1}^{\#-1} g_i (s_i - z_i + z_{i+1} - t_i)^2 + h(l + z_{k+1} - z_k - r)^2$$

Where:
# is the number of the tooth;
$w_i$ is the weight of tooth movement;
$z_i$ is the movement of tooth i to next tooth along the archform;
$g_i$ is the weight of space/IPR between tooth i and i+1;
$s_i$ is the current space/IPR for tooth i;
$t_i$ is the space/IPR assigned between tooth i and i+1;
$s_i - z_i + z_{i+1}$ is the space/IPR after the tooth is moved;
h is the weight of midline shift;
l is the current midline shift;
r is the setup value of midline shift; and
$z_k$, $z_{k+1}$ are the movement of two middle incisors.

In general, greater weights indicate that the parameter will be complied with more, while lesser weights mean that the parameter is less stringent on the overall outcome. If a particular weight is infinitely large, the corresponding parameter must be set to the assigned value. If the weight is zero, the corresponding parameter can be set to any value or free to change.

For example with respect to tooth mobility, the weights can be set to $w_i=0.01$, if the tooth is free to move or $w_i=1,000,000$ if the tooth is not movable or is an anchorage. For example with respect to space/IPR:

- $g_i$ can be set to 10,000 and $t_i$ can be set to −0.1 if there is contact (e.g., 0.1 mm overlap between the teeth);
- $g_i$ can be set to 10,000 and $t_i$ can be set to 2.0 if there is 2 mm left for this contact;
- $g_i$ can be set to 10,000 and $t_i$ can be set to −0.75 if there is a 0.75 mm IPR assigned;
- $g_i$ can be set to 1 and $t_i$ can be set to 0.0 if normal space and/or IPR can be assigned;
- $g_i$ can be set to 0.5 and $t_i$ can be set to 0.0 if more normal space and/or IPR an be assigned; or
- $g_i$ can be set to 0.25 and $t_i$ can be set to 0.0 if a maximum amount of space and/or IPR is allowed.

For example with respect to midline shift, h can be set to 10,000 and r can be set to 2.0 if the midline shift is set to 2 mm or h can be set to 0.000001 if the midline shift is not set and/or is free to change. The above examples can be combined to implement a number of different setups and/or algorithms.

An example of automatic IPR setup can include setting the last molars as anchorages, while other teeth are free to move. If there is any space between teeth, all teeth can be set to contact (e.g., leaving 0.1 mm overlap between two teeth) and the space assigned to the mesial side of the canine can be set by $g_i=0.25$ and $t_i=0.0$. If the total IPR is between 0 and 0.8 mm, the IPR can be assigned to the mesial side of the canine by a greater amount, such as $g_i=0.25$ and $t_i=0.0$, and between incisors by a lesser amount, such as $g_i=1.0$ and $t_i=0.0$. If the total IPR is greater than 0.8 mm, the IPR can be assigned to the canine, incisors, and premolars by $g_i=0.25$ and $t_i=0.0$, $g_i=0.5$ and $t_i=0.0$, and $g_i=1.0$ and $t_i=0.0$, respectively.

For example, in FIG. 9, the last molar 936 can be set as an anchorage. The total IPR for this virtual dental model 951 is 2.96 mm, which is greater than 0.8 mm, therefore IPR can be assigned to the canine, incisors, premolars, and molars. An example result of optimizing the function can result in IPR values assigned as: 0.00 mm between the last molar and an adjacent molar as indicated by IPR 935-1, 0.60 mm between two molars and between a premolar and molar as indicated respectively by IPR 935-2 and IPR 935-3, 1.00 mm between the premolars as indicated by IPR 935-4, and 0.38 mm between the canine and premolar and between the incisor and canine as indicated respectively by IPR 935-5 and IPR 935-6.

Once IPR values have been assigned in the virtual dental model, the teeth can be adjusted in the archform accordingly. Because movement in the archform may alter the spacing and/or crowding between adjacent teeth, several iterations of optimization of the function may be performed to reach a stable and/or desirable result. Such iterations may include computing space, crowding, and midline shift, optimizing the function to adjust the teeth, moving the teeth in the archform for a certain percentage (e.g., 90%) of the result computed from optimizing the function, and repeating the process until the amount of movement and/or IPR for each tooth is within specified thresholds of acceptability. In some embodiments, for a particular tooth, IPR can be assigned to one side of the tooth, while any spacing is closed for the other side of the tooth. In various embodiments, IPR can be computed for portions of a posterior tooth that has collisions remaining after the adjustment according to a last iteration.

Figure 10:
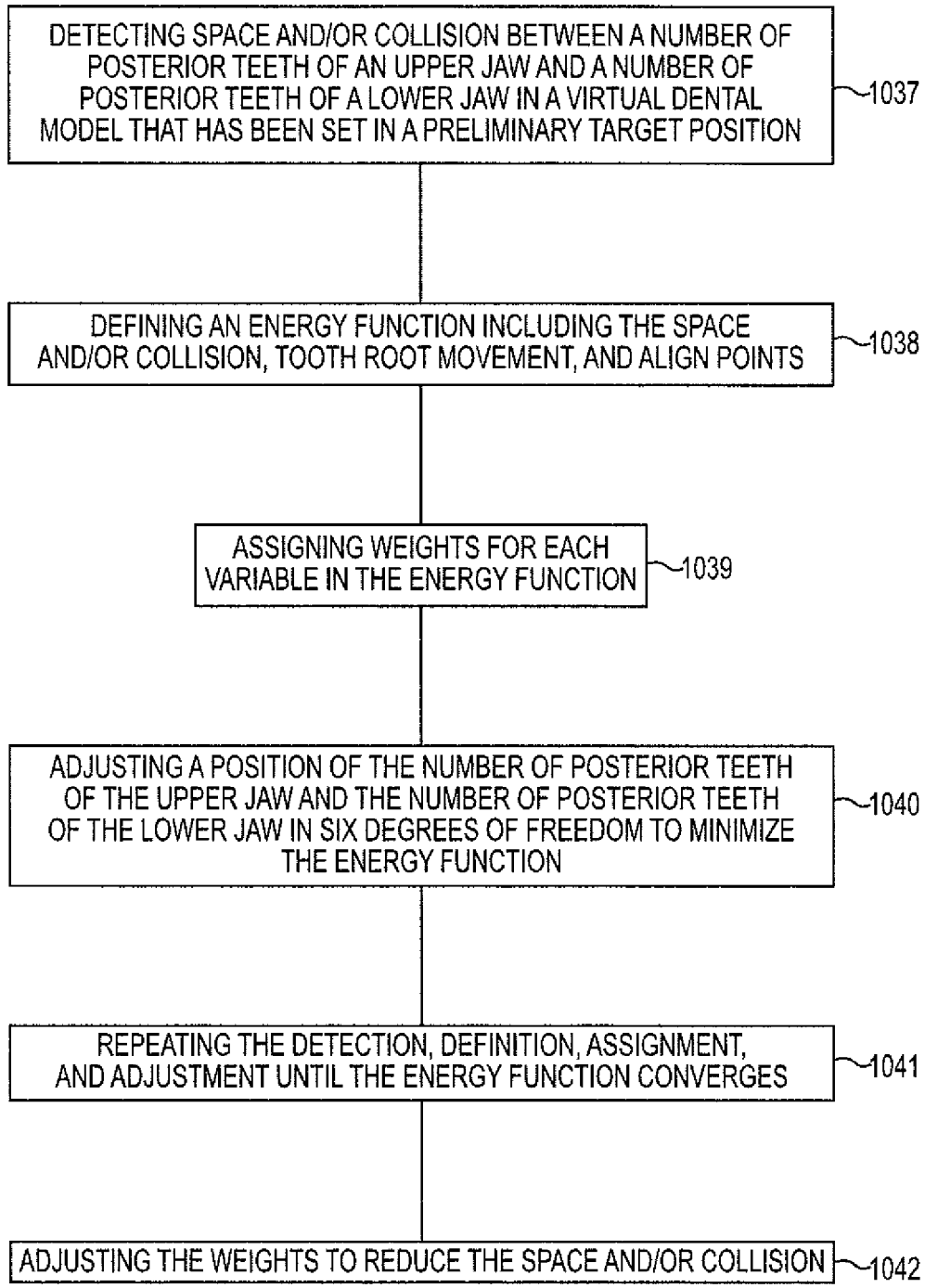
FIG. 10 is a flow chart illustrating a method for adjustment of tooth position in a virtual dental model according to one or more embodiments of the present disclosure.

FIG. 10 is a flow chart illustrating a method for adjustment of tooth position in a virtual dental model according to one or more embodiments of the present disclosure. At 1037 the method can include detecting space and/or collision between a number of posterior teeth of an upper jaw and a number of posterior teeth of a lower jaw in a virtual dental model that has been set in a preliminary target position. In some embodiments, the preliminary target position can be manually defined by a user. In a number of embodiments, the preliminary target position can be automatically defined by the computing device.

At 1038 the method can include defining an energy function including the space and/or collision, tooth root movement, and align points. At 1039 the method can include assigning weights for each variable in the energy function. An example of an energy function and accompanying assignment of weights is described above with respect to FIG. 8. At 1040 the method can include adjusting a position of the number of posterior teeth of the upper jaw and the number of posterior teeth of the lower jaw in six degrees of freedom to minimize the energy function.

At 1041 the method can include repeating the detection, definition, assignment, and adjustment until the energy function converges. At 1042 the method can include adjusting the weights (e.g., after the energy function converges) to reduce the space and/or collision.

In some embodiments, the position of the teeth after convergence of the energy function and/or adjustment of the weights can be defined as the final target position. In a number of embodiments, a user can manually adjust the position of a number of teeth after the energy function converges to further refine the occlusion. Such embodiments may provide advantages over some previous approaches by reducing the amount of manual adjustment required to achieve a desired final target position. In such embodiments, the position after convergence and manual adjustment can be defined as the final target position.

The method can include defining a number of treatment steps between the preliminary target position and a final target position for each of the upper jaw and the lower jaw based on the converged energy function, wherein each of the number of treatment steps corresponds to an amount of adjustment to be performed by an orthodontic appliance. A series of incremental dental position adjustment appliances can be designed to correspond to the number of treatment steps (e.g., automatically by software).

Figure 11:
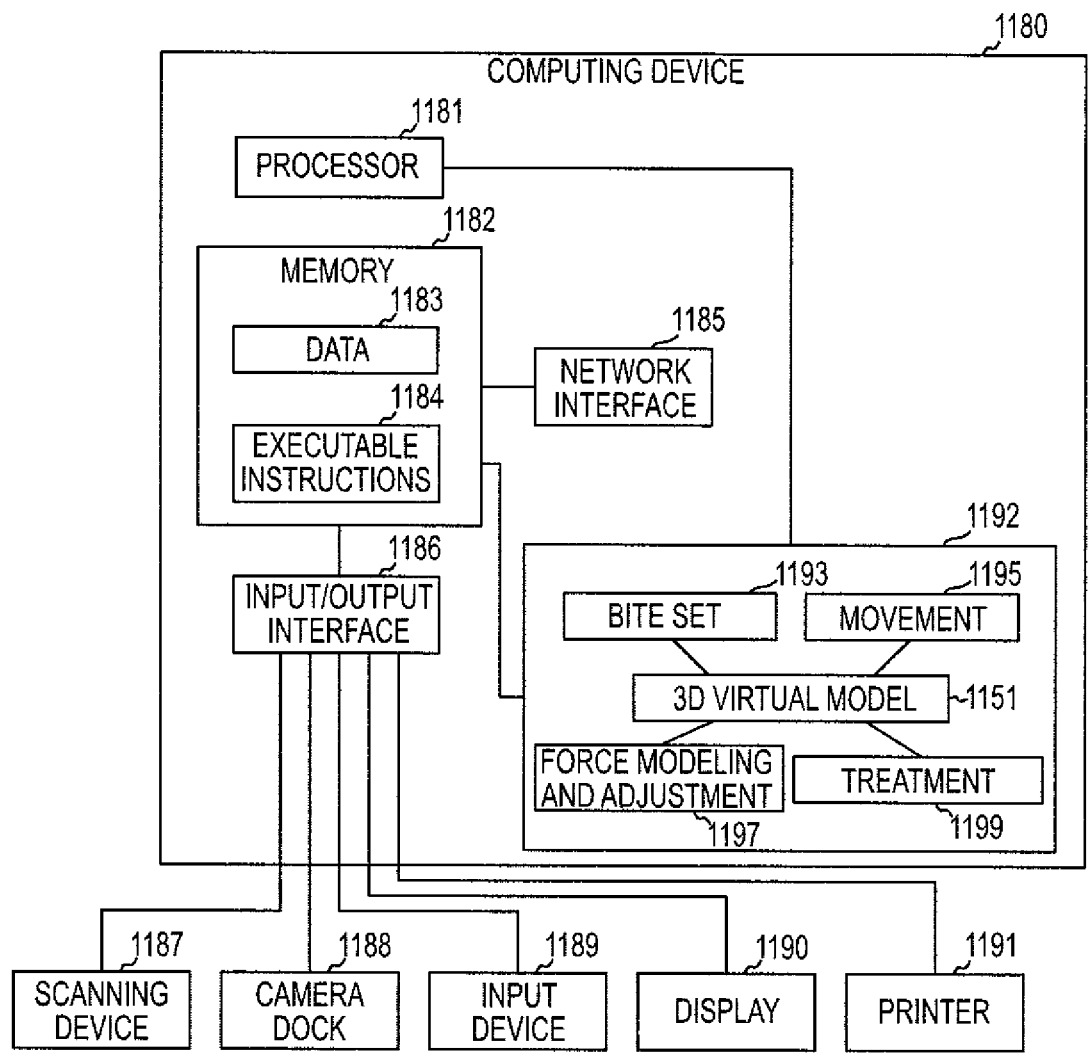
FIG. 11 illustrates a system for adjustment of tooth position in a virtual dental model according to one or more embodiments of the present disclosure.

FIG. 11 illustrates a system for adjustment of tooth position in a virtual dental model according to one or more embodiments of the present disclosure. In the system illustrated in FIG. 11, the system includes a computing device 1180 having a number of components coupled thereto. The computing device 1180 includes a processor 1181 and memory 1182. The memory can include various types of information including data 1183 and executable instructions 1184 as discussed herein.

Memory and/or the processor may be located on the computing device 1180 or off the device in some embodiments. As such, as illustrated in the embodiment of FIG. 11, a system can include a network interface 1185. Such an interface can allow for processing on another networked computing device or such devices can be used to obtain information about the patient or executable instructions for use with various embodiments provided herein.

As illustrated in the embodiment of FIG. 11, a system can include one or more input and/or output interfaces 1186. Such interfaces can be used to connect the computing device with one or more input or output devices.

For example, in the embodiment illustrated in FIG. 11, the system includes connectivity to a scanning device 1187, a camera dock 1188, an input device 1189 (e.g., a keyboard, mouse, etc.), a display device 1190 (e.g., a monitor), and a printer 1191. The input/output interface 1186 can receive data, storable in the data storage device (e.g., memory 1182), representing the virtual dental model 1151 corresponding to the patient's upper jaw and the patient's lower jaw.

In some embodiments, the scanning device 1187 can be configured to scan a physical mold of a patient's upper jaw and a physical mold of a patient's lower jaw. In one or more embodiments, the scanning device 1187 can be configured to scan the patient's upper and/or lower jaws directly.

The camera dock 1188 can receive an input from an imaging device (e.g., a 2D imaging device) such as a digital camera or a printed photograph scanner. The input from the imaging device can be stored in the data storage device 1182.

The processor 1181 can be configured to provide a visual indication of a virtual dental model 1151 on the display 1190 (e.g., on a GUI running on the processor 1181 and visible on the display 1190).

Such connectivity can allow for the input and/or output of virtual dental model information or instructions (e.g., input via keyboard) among other types of information. Although some embodiments may be distributed among various computing devices within one or more networks, such systems as illustrated in FIG. 11 can be beneficial in allowing for the capture, calculation, and/or analysis of information discussed herein.

The processor 1181, in association with the data storage device 1182, can be associated with data and/or application modules 1192. The processor 1181, in association with the data storage device 1182, can store and/or utilize data and/or execute instructions to provide a number of application modules for virtual dental modeling.

Such data can include the 3D virtual dental model 1151 described herein (e.g., including a first jaw and a second jaw). Such application modules can include a bite set module 1193, a movement module 1195, a force modeling and adjustment module 1197, and/or a treatment module 1199.

The bite set module 1193 can be configured to bite set a first jaw and a second jaw in the virtual dental model 1151. The movement module 1195 can be configured to move the first jaw toward the second jaw in the virtual dental model 1151 from the bite set position (e.g., to set the teeth in respectively close positions under the influence of collision forces similar to a chewing process). If the teeth are not inconsistent and/or misaligned, the pressure should be distributed with some degree of uniformity across the teeth. However, if there are inconsistent and/or misaligned teeth, there may be a less uniform distribution of pressure.

The force modeling and adjustment module 1197 can be configured to model a number of repulsive forces for collisions between a number of points in the first jaw and a respective number of points in the second jaw in the virtual dental model 1151. The repulsive forces can be modeled in response to the first jaw being moved toward the second jaw from the bite set position (e.g., in response to the jaws having increased tooth contact). In some embodiments, the force modeling does not include attractive forces between opposite jaws or between teeth in opposite jaws.

The force modeling and adjustment module 1197 can be configured to identify one of the number of repulsive forces having a magnitude that is different than others of the number of repulsive forces by a statistically significant amount. The repulsive forces can be generated according to collisions between teeth in opposite jaws that arise from the first jaw being moved toward the second jaw. The one of the number of repulsive forces having the statistically significant different magnitude can indicate one or more corresponding teeth that are preventing good occlusion for the virtual dental model 1151.

The force modeling and adjustment module 1197 can be configured to determine a positional adjustment to one of the number of points corresponding to the statistically significantly different repulsive force to reduce the difference. The force modeling and adjustment module 1197 can be configured to assign a first allocation of the positional adjustment to the tooth including the one of the number of points and to assign a second allocation of the positional adjustment to one of the first jaw and the second jaw including the tooth. Thus, the tooth presumed to be preventing good occlusion can be "corrected" first.

The force modeling and adjustment module 1197 can be configured to limit the second allocation based on a range of motion of the one of the first jaw and the second jaw. The force modeling and adjustment module 1197 can be configured to maximize the second allocation within the limit of the range of motion.

The treatment module 1199 can be configured to define a number of treatment steps between a first arrangement of teeth in the first jaw and the second jaw and a second arrangement of teeth in the first jaw and the second jaw based on the positional adjustment.

The system 1180 can be further configured to iteratively move the first jaw toward the second jaw, model the number of repulsive forces, identify one of the number of repulsive forces, determine a positional adjustment, and assign a first and a second allocation of the positional adjustment. Thus, as the system 1180 progresses after correcting one tooth that may be preventing good occlusion, it can make an adjustment, and identity and correct another tooth that may be preventing good occlusion.

The system 1180 can be further configured to iterate until none of the number of repulsive forces have a magnitude that is different than others of the number of repulsive forces by a statistically significant amount. That is, the system 1180 can automatically achieve a desirable final position for the teeth in the virtual dental model 1151.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A computing device readable physical medium having instructions which can be executed by a processor to cause a computing device to:
   generate a virtual dental model that includes an upper jaw and a lower jaw;
   calculate a number of current feature splines for each of the upper jaw and the lower jaw of the virtual dental model;
   calculate a number of target feature splines based on interaction between the number of current feature splines for the upper jaw and the lower jaw;
   model an attractive force on the virtual dental model, wherein the attractive force encourages movement of a feature point on one of the number of current feature splines to a corresponding feature point on a corresponding one of the number of target feature splines;
   model a repulsive force on the virtual dental model, wherein the repulsive force is generated according to collisions between a point in upper jaw and a point in the lower jaw that arise from the first jaw being moved toward the second jaw;
   model a stabilization force on the virtual dental model, wherein the stabilization force matches pairs of points within one of the upper jaw and the lower jaw to limit motion of a tooth to be within a range of motion within one of the upper jaw and the lower jaw;
   define a number of orthodontic treatment steps by moving between the number of current feature splines and the number of target feature splines for each of the upper jaw and the lower jaw based on the attractive force, the repulsive force, and the stabilization force; and
   communicate data for forming a set of orthodontic appliances in accordance with the number of orthodontic treatment steps to a fabrication device configured to form the set of orthodontic appliances.

2. The medium of claim 1, wherein the instructions further cause the computing device to:
   determine a number of feature points for each of a number of posterior teeth of the upper jaw and a number of posterior teeth of the lower jaw; and
   calculate the number of current feature splines based on the determined number of feature points.

3. The medium of claim 2, wherein each of the number of feature points correspond to cusps or grooves.

4. The medium of claim 2, wherein the instructions further cause the computing device to model respective attractive forces between each of the number of feature points on the one of the number of current feature splines and each of the corresponding number of feature points on the one of the number of target feature splines.

5. The medium of claim 2, wherein the instructions further cause the computing device to model respective repulsive forces between any points in the upper jaw and any points in the lower jaw that are in collision in the virtual dental model.

6. The medium of claim 2, wherein the instructions further cause the computing device to model respective stabilization forces to limit motion of teeth in the virtual dental model to be within respective ranges of motion.

7. The medium of claim 1, wherein the instructions cause the computing device to model a first stabilization force for tooth rotation and a second stabilization force for tooth translation.

8. The medium of claim 1, wherein the instructions cause the computing device to model the stabilization force as a force acting on a point in the virtual dental model that reduces movability of the point as other forces are applied to the virtual dental model.

9. The medium of claim 1, wherein the instructions further cause the computing device to incrementally define teeth position by incrementally applying the attractive force, the repulsive force, and the stabilization force.

10. The medium of claim 9, wherein the instructions further cause the computing device to adjust a weighting of one or more of the attractive force, the repulsive force, and the stabilization force after each application thereof such that an increment of tooth movement for each tooth in the virtual dental model is within a respective tolerance.

11. The medium of claim 1, wherein the corresponding feature point on the corresponding one of the number of target feature splines comprises the feature point on the one of the number of current feature splines projected to the corresponding one of the number of target feature splines.

12. The medium of claim 1, wherein the upper jaw and the lower jaw of the virtual dental model are aligned prior to calculation of the number of current feature splines.

13. A computing device readable physical medium having instructions which can be executed by a processor to cause a computing device to:
   generate a virtual dental model that includes an upper jaw and a lower jaw;
   calculate a number of current feature splines for each of the upper jaw and the lower jaw of the virtual dental model;
   calculate a number of target feature splines based on interaction between the number of current feature splines for the upper jaw and the lower jaw of the virtual dental model;
   model an attractive force on the virtual dental model, wherein the attractive force encourages movement from a feature point on one of the number of current feature splines to a corresponding feature point on a corresponding one of the number of target feature splines;

model a repulsive force on the virtual dental model, wherein the repulsive force is generated according to collisions between a point in upper jaw and a point in the lower jaw that arise from the first jaw being moved toward the second jaw;

model a stabilization force on the virtual dental model, wherein the stabilization force matches pairs of points within one of the upper jaw and the lower jaw to limit motion of a tooth to be within a range of motion within one of the upper jaw and the lower jaw;

define a number of treatment steps between the number of current feature splines and the target feature splines for each of the upper jaw and the lower jaw based on the attractive force and the stabilization force;

redefine the number of orthodontic treatment steps by moving between the number of current feature splines and the number of target feature splines for each of the upper jaw and the lower jaw based on the repulsive force and the stabilization force; and communicate data for forming a set of orthodontic appliances in accordance with the number of orthodontic treatment steps to a fabrication device configured to form the set of orthodontic appliances.

14. The medium of claim 13, wherein the instructions further cause the computing device to:

determine a number of feature points for each of a number of posterior teeth of the upper jaw and a number of posterior teeth of the lower jaw, wherein each of the number of feature points correspond to cusps or grooves; and calculate the number of current feature splines based on the determined number of feature points.

15. The medium of claim 14, wherein the instructions further cause the computing device to:

model respective attractive forces between each of the number of feature points on the one of the number of current feature splines and each of the corresponding number of feature points on the one of the number of target feature splines; and model respective repulsive forces between any points in the upper jaw and any points in the lower jaw that are in collision in the virtual dental model.

16. The medium of claim 13, wherein the instructions further cause the computing device to:

incrementally define the number of treatment steps between the number of current feature splines and the target feature splines by incrementally applying the attractive force and the stabilization force; and incrementally redefine the number of treatment steps between the number of current feature splines and the target feature splines by incrementally applying the repulsive force and the stabilization force.

17. The medium of claim 16, wherein the instructions further cause the computing device to adjust a weighting of one or more of the attractive force, the repulsive force, and the stabilization force after each application thereof such that an increment of tooth movement for each tooth in the virtual dental model is within a respective tolerance.

18. A computing device implemented method, comprising:

generating a virtual dental model that includes an upper jaw and a lower jaw;

calculating a number of current feature splines for each of the upper jaw and the lower jaw of the virtual dental model;

calculating a number of target feature splines based on interaction between the number of current feature splines for the upper jaw and the lower jaw of the virtual dental model;

modeling an attractive force on the virtual dental model, wherein the attractive force encourages movement of a feature point on one of the number of current feature splines to a corresponding feature point on a corresponding one of the number of target feature splines;

modeling a repulsive force on the virtual dental model, wherein the repulsive force is generated according to collisions between a point in upper jaw and a point in the lower jaw that arise from the first jaw being moved toward the second jaw;

modeling a stabilization force on the virtual dental model, wherein the stabilization force matches pairs of points within one of the upper jaw and the lower jaw to limit motion of a tooth to be within a range of motion within one of the upper jaw and the lower jaw;

defining a number of orthodontic treatment steps by moving between the number of current feature splines and the number of target feature splines for each of the upper jaw and the lower jaw based on the attractive force, the repulsive force, and the stabilization force; and forming a set of orthodontic appliances in accordance with the number of orthodontic treatment steps.

19. The method of claim 18, further comprising:

determining a number of feature points for each of a number of posterior teeth of the upper jaw and a number of posterior teeth of the lower jaw; and calculating the number of current feature splines based on the determined number of feature points.

20. The method of claim 18, further comprising incrementally defining teeth position by incrementally applying the attractive force, the repulsive force, and the stabilization force.

* * * * *